US010927116B2

United States Patent
Chen

(10) Patent No.: US 10,927,116 B2
(45) Date of Patent: Feb. 23, 2021

(54) PROCESS FOR THE PREPARATION OF 4-PHENYL-5-ALKOXYCARBONYL-2-THIAZOL-2-YL-1,4-DIHYDROPYRIMIDIN-6-YL]METHYL]-3-OXO-5,6,8,8A-TETRAHYDRO-1H-IMIDAZO[1,5-A]PYRAZIN-2-YL]-CARBOXYLIC ACID

(71) Applicant: Hoffmann-La Roche Inc., Little Falls, NJ (US)

(72) Inventor: Junli Chen, Shanghai (CN)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 15/999,701

(22) Filed: Aug. 20, 2018

(65) Prior Publication Data

US 2019/0010155 A1  Jan. 10, 2019

Related U.S. Application Data

(63) Continuation of application No. PCT/EP2017/053443, filed on Feb. 16, 2017.

(30) Foreign Application Priority Data

Feb. 19, 2016  (WO) ............... PCT/CN2016/074132

(51) Int. Cl.
C07D 487/04  (2006.01)
(52) U.S. Cl.
CPC ................... C07D 487/04 (2013.01)
(58) Field of Classification Search
CPC ...................................................... C07D 487/04
See application file for complete search history.

(56) References Cited

U.S. PATENT DOCUMENTS

2015/0252057 A1* 9/2015 Guo .................. A61K 31/4985
514/230.5
2016/0083383 A1  3/2016 Guo et al.

FOREIGN PATENT DOCUMENTS

| CN | 101041658 A | 9/2007 |
|---|---|---|
| WO | 2001/68640 A1 | 9/2001 |
| WO | 2002/094807 A1 | 11/2002 |
| WO | 2010/069147 A1 | 6/2010 |
| WO | 2014/029193 A1 | 2/2014 |
| WO | 2014/037480 A1 | 3/2014 |
| WO | 2014/184328 A1 | 11/2014 |
| WO | 2015/132276 A1 | 9/2015 |
| WO | 2016/016196 A1 | 2/2016 |
| WO | 2016/102438 A1 | 6/2016 |

OTHER PUBLICATIONS

International Search Report and Written Opinion for PCT/EP2017/053443 (dated Mar. 24, 2017).
Malancona et al., "Identification of MK-5710 ((8aS)-8a-methyl-1,3-dioxo-2-[(1S,2R)-2-phenylcyclopropyl]-N-(1-phenyl-1H-pyrazol-5-yl)hexahydroimid azo[1,5-a]pyrazine-7(1H)-carboxamide), a potent smoothened antagonist for use in Hedgehog pathway dependent malignancies, Part 1" Bioorganic & Medicinal Chemistry Letters 21(15):4422-4428 ( 2011).

\* cited by examiner

*Primary Examiner* — Emily A Bernhardt
(74) *Attorney, Agent, or Firm* — Genentech, Inc.; Richard G. A. Bone

(57) ABSTRACT

The present invention relates to a process for synthesizing a compound of formula (I),

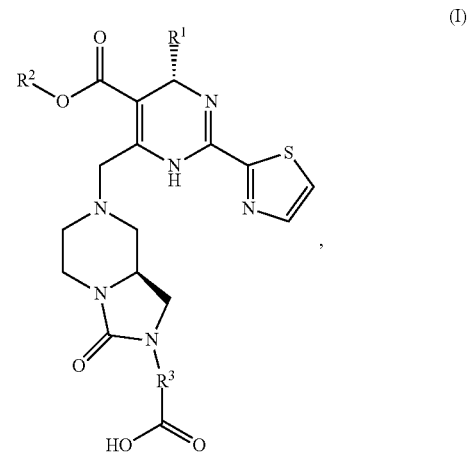

$R^1$ is phenyl, which is unsubstituted or substituted with one, two or three substituents independently selected from halogen and $C_{1-6}$alkyl; $R^2$ is $C_{1-6}$alkyl; $R^3$ is $-C_xH_{2x}-$; x is 1, 2, 3, 4, 5, 6 or 7; or pharmaceutically acceptable salt or diastereomer thereof, which is useful for prophylaxis and treatment of a viral disease in a patient relating to hepatitis B infection or a disease caused by hepatitis B infection.

66 Claims, 1 Drawing Sheet

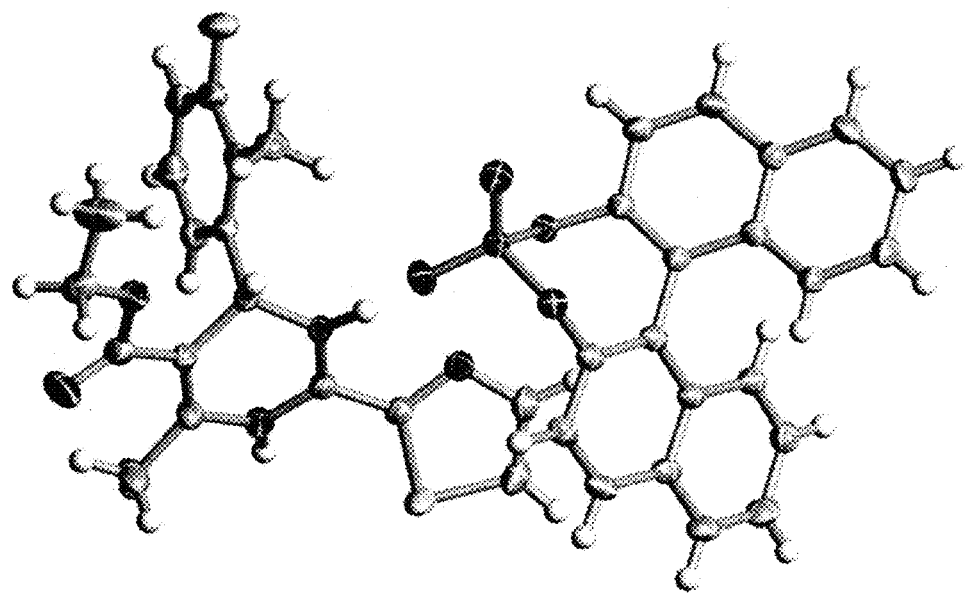

PROCESS FOR THE PREPARATION OF 4-PHENYL-5-ALKOXYCARBONYL-2-THIAZOL-2-YL-1,4-DIHYDROPYRIMIDIN-6-YL]METHYL]-3-OXO-5,6,8,8A-TETRAHYDRO-1H-IMIDAZO[1,5-A]PYRAZIN-2-YL]-CARBOXYLIC ACID

RELATED APPLICATIONS

This application is a continuation of International Application No. PCT/EP2017/053443, filed Feb. 16, 2017 claiming priority to Application No. PCT/CN2016/074132 filed Feb. 19, 2016, each of which are incorporated herein by reference in its entirety.

The present invention relates to a process for the preparation of a compound of formula (Ia),

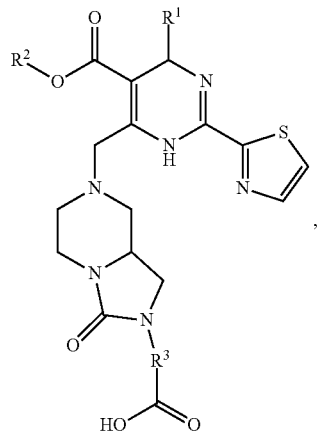

particularly a compound of formula (I),

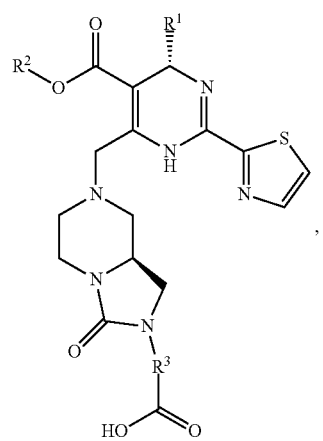

wherein
$R^1$ is phenyl, which is unsubstituted or substituted with one, two or three substituents independently selected from halogen and $C_{1-6}$alkyl;
$R^2$ is $C_{1-6}$alkyl;
$R^3$ is —$C_xH_{2x}$—;
x is 1, 2, 3, 4, 5, 6 or 7;
or pharmaceutically acceptable salt or diastereomer thereof, which is useful for prophylaxis and treatment of a viral disease in a patient relating to hepatitis B infection or a disease caused by hepatitis B infection.

BACKGROUND OF THE INVENTION

The synthetic approach of compounds of formula (I) was disclosed in patent WO2015132276, however it is not suitable for commercial process due to the following issues:
(a) the overall yield is very low (0.2-0.4%);
(b) qualified starting material (tert-butyl (3S)-3-(hydroxymethyl)piperazine-1-carboxylate) in large quantity is not commercially available;
(c) column purification is needed for four of the intermediates, such as: O1-benzyl O4-tert-butyl (2S)-2-(hydroxymethyl)piperazine-1,4-dicarboxylate; O1-benzyl O4-tert-butyl (2R)-2-[[(3-ethoxy-2,2-dimethyl-3-oxo-propyl)amino]methyl]piperazine-1,4-dicarboxylate (partly or all racemic); tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate and ethyl (4S)-6-(bromomethyl)-4-(3-fluoro-2-methyl-phenyl)-2-thiazol-2-yl-1,4-dihydropyrimidine-5-carboxylate;
(d) two key intermediates, ethyl 4-(3-fluoro-2-methyl-phenyl)-6-methyl-2-thiazol-2-yl-1,4-dihydropyrimidine-5-carboxylate and tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate, are racemic or partly racemic, therefore chiral HPLC or chiral SFC is required for chiral purification of the intermediates or final API;
(e) Swern oxidation is not robust for large scale, which usually works on small scale with potential racemization issue;
(f) 3-[(8aS)-3-oxo-1,5,6,7,8,8a-hexahydroimidazo[1,5-a]pyrazin-2-yl]-2,2-dimethyl-propanoic acid (TFA salt, containing massive inorganic salt) is a sticky semi-solid, causing poor conversion and more impurities in final step, which leads to HPLC purification for the final API.

Based on the issues above, one object of the invention therefore is to find an alternative efficient synthetic approach which can be applied on a technical scale and/or result in obtaining the product in a higher yield and/or desired purity. Addressing any of the issues (a) to (f) mentioned above is also one of the objects of the invention.

Another aspect of the present invention relates to a novel process for the preparation of a compound of the formula (X):

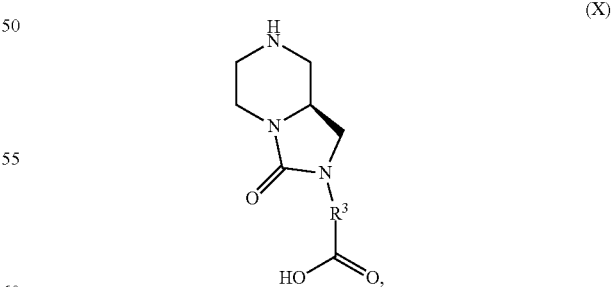

wherein $R^3$ is —$C_xH_{2x}$—; x is 1, 2, 3, 4, 5, 6 or 7; or pharmaceutically acceptable salt, enantiomer or diastereomer thereof.

Compound of the formula (X) is a key intermediate in the synthesis and manufacture of pharmaceutically active compound of formula (I) as described herein.

DETAILED DESCRIPTION OF THE INVENTION

Definitions

As used herein, the term "$C_{1-6}$alkyl" signifies a saturated, linear- or branched chain alkyl group containing 1 to 6, particularly 1 to 5 carbon atoms, for example methyl, ethyl, n-propyl, isopropyl, n-butyl, isobutyl, tert-butyl and the like. Particular "$C_{1-6}$alkyl" group is methyl or ethyl.

The term "halogen" signifies fluorine, chlorine, bromine or iodine, particularly fluorine or chlorine.

The term "diastereomer" denotes a stereoisomer with two or more centers of chirality and whose molecules are not mirror images of one another.

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such asp-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457.

BRIEF DESCRIPTION OF THE FIGURES

FIG. 1. X-ray structure of Example 9.

ABBREVIATION

ACN Acetonitrile
API active pharmaceutical ingredient
Boc tert-Butoxycarbonyl
(R)—BNP acid (R)-(−)-1,1'-Binaphthyl-2,2'-diyl hydrogen phosphate
CPME Cyclopentyl methyl ether
DBU 1,8-Diazabicyclo[5.4.0]undec-7-ene
DIPEA N,N-Diisopropylethylamine
eq Equivalent
GABA γ-aminobutyric acid
IPA Isopropanol
IPAc Isopropyl acetate
EtOAc or EA ethyl acetate
MEK 2-Butanone
2-MeTHF 2-Methyltetrahydrofuran
MIBK Methyl isobutyl ketone
MSA Methanesulfonic acid
MTBE Methyl tert-butyl ether
NBS N-bromosuccinimide
NMM N-methylmorpholine
TEA Triethylamine
TFA Trifluoroacetic acid
TMP 2,2,6,6-Tetramethylpiperidine
v/v Volume ratio
V65 2,2'-Azobis-(2,4-dimethylvaleronitrile)
wt % Weight percentage The present invention provides a process for preparing the compounds of formula (X) as outlined in the scheme 1 and compounds of formula (I) as outlined in the scheme 2.

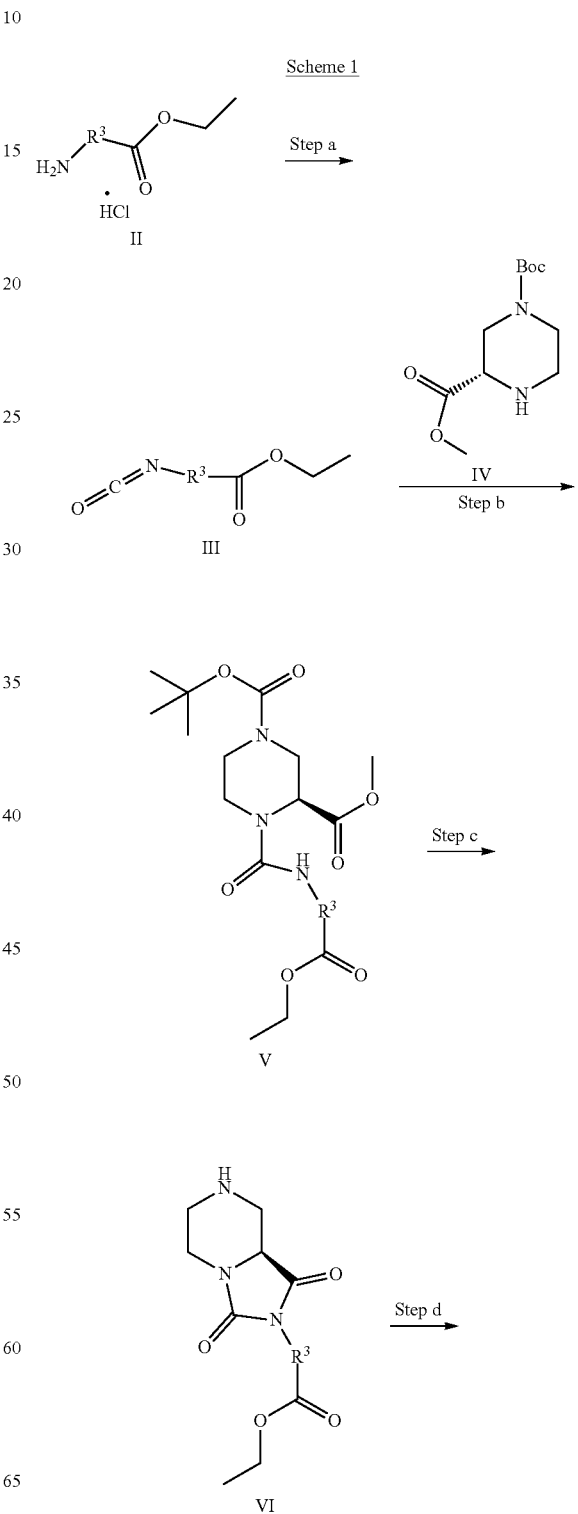

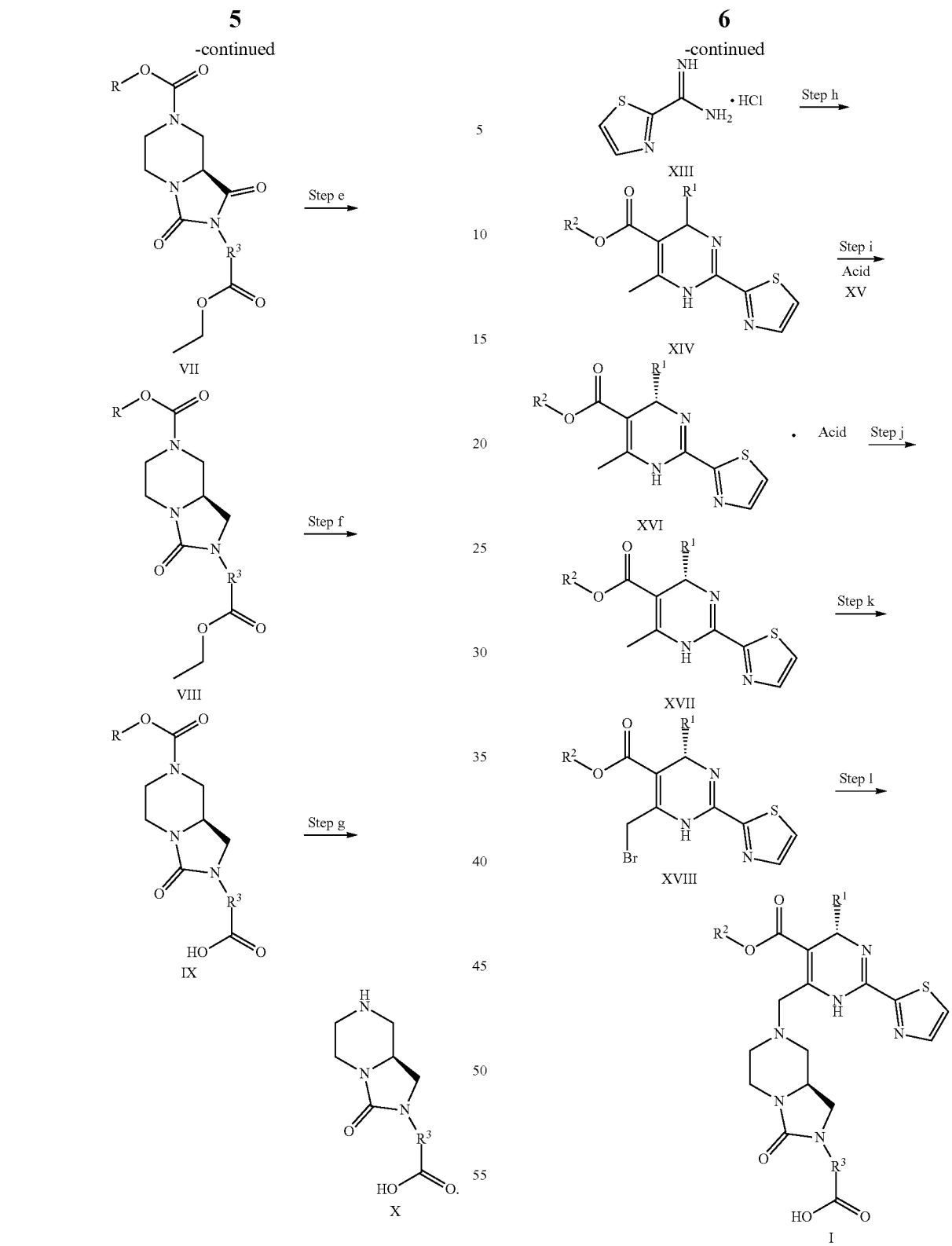
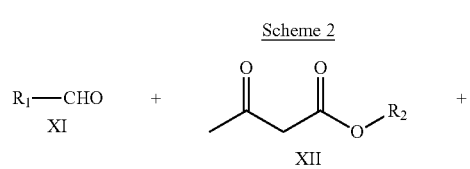
wherein $R^1$ is phenyl, which is unsubstituted or substituted with one, two or three substituents independently selected from halogen and $C_{1-6}$alkyl; $R^2$ is $C_{1-6}$alkyl; $R^3$ is —CH$_2$—; x is 1, 2, 3, 4, 5, 6 or 7; R is $C_{1-6}$ alkyl; Acid is D-(+)-DTTA, L-DTTA, L-Tartaric acid, D-DBTA, (+)-CSA, (S)-(+)-1,1'-Binaphthyl-2,2'-diyl hydrogen phosphate or (R)-(−)-1,1'-Binaphthyl-2,2'-diyl hydrogen phosphate.

The synthesis comprises one or more of the following steps:

step a) the formation of the isocyanate (III),

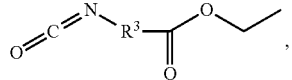
(III)

wherein R³ is —C$_x$H$_{2x}$—; x is 1, 2, 3, 4, 5, 6 or 7;

step b) the formation of urea (V) via the addition reaction of isocyanate (III) and compound (IV),

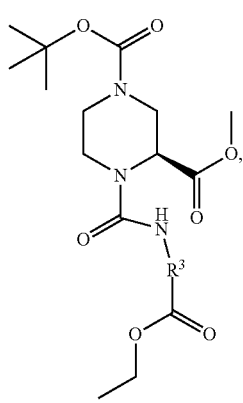
(V)

wherein R³ is —C$_x$H$_{2x}$—; x is 1, 2, 3, 4, 5, 6 or 7;

step c) the formation of the compound of formula (VI) via the cyclization reaction of urea (V),

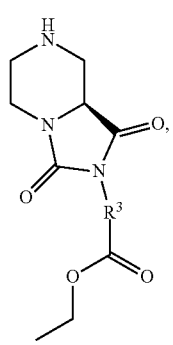
(VI)

wherein R³ is —C$_x$H$_{2x}$—; x is 1, 2, 3, 4, 5, 6 or 7;

step d) the formation of the compound of formula (VII) by protection of the compound of formula (VI),

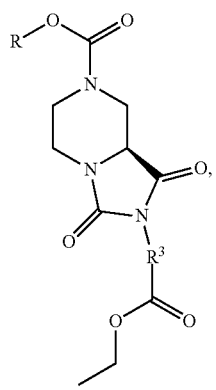
(VII)

wherein R³ is —C$_x$H$_{2x}$—; x is 1, 2, 3, 4, 5, 6 or 7; R is C$_{1-6}$alkyl;

step e) the formation of the compound of formula (VIII) via selective reduction of the compound of formula (VII),

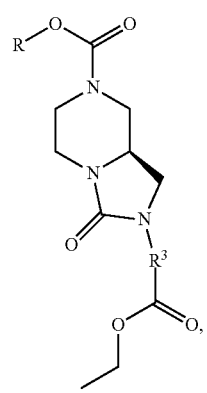
(VIII)

wherein R³ is —C$_x$H$_{2x}$—; x is 1, 2, 3, 4, 5, 6 or 7; R is C$_{1-6}$alkyl;

step f) the formation of the compound of formula (IX) via hydrolysis of the compound of formula (VIII),

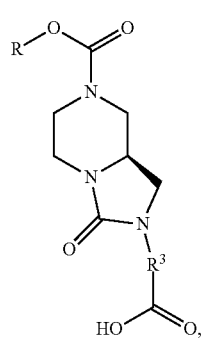
(IX)

wherein R³ is —C$_x$H$_{2x}$—; x is 1, 2, 3, 4, 5, 6 or 7; R is C$_{1-6}$alkyl;

step g) the formation of compound of formula (X) by de-protection of the compound of formula (IX),

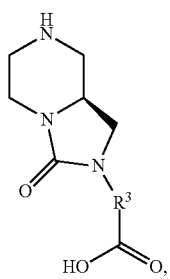

(X)

wherein R³ is —C$_x$H$_{2x}$—; x is 1, 2, 3, 4, 5, 6 or 7;
step h) the formation of compound of formula (XIV) via Biginelli-like reaction,

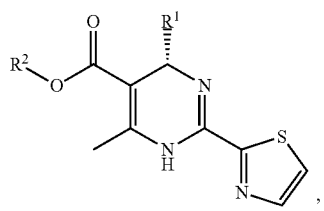

(XIV)

wherein R¹ is phenyl, which is unsubstituted or substituted with one, two or three substituents independently selected from halogen and C$_{1-6}$alkyl; R² is C$_{1-6}$alkyl;
step i) the formation and recrystallization of the enantiomeric salt of compound of formula (XVI) or solvate,

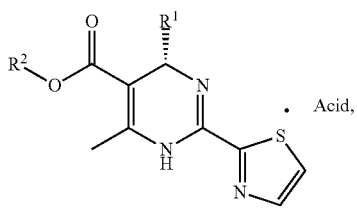

(XVI)

· Acid, wherein R¹ is phenyl, which is unsubstituted or substituted with one, two or three substituents independently selected from halogen and C$_{1-6}$alkyl; R² is C$_{1-6}$alkyl; acid is D-(+)-DTTA, L-DTTA, L-Tartaric acid, D-DBTA, (+)-CSA, (S)-(+)-1,1'-Binaphthyl-2,2'-diyl hydrogen phosphate or (R)-(−)-1,1'-Binaphthyl-2,2'-diyl hydrogen phosphate;
step j) the recovery of enantiomeric compound of formula (XVII) from its enantiomeric salt of formula (XVI) or solvate,

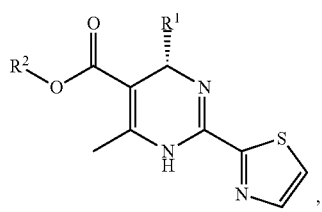

(XVII)

wherein R¹ is phenyl, which is unsubstituted or substituted with one, two or three substituents independently selected from halogen and C$_{1-6}$alkyl; R² is C$_{1-6}$alkyl;
step k) the formation of compound of formula (XVIII) via the bromination reaction of compound of formula (XVII),

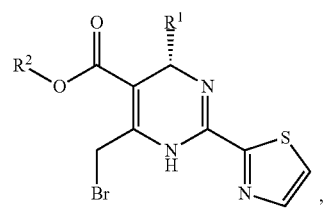

(XVIII)

wherein R¹ is phenyl, which is unsubstituted or substituted with one, two or three substituents independently selected from halogen and C$_{1-6}$alkyl; R² is C$_{1-6}$alkyl;
step l) the formation of compound of formula (I) via the substitution reaction of compound of formula (XVIII) with compound of formula (X),

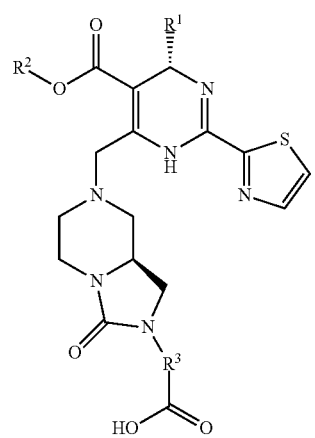

(I)

wherein R¹ is phenyl, which is unsubstituted or substituted with one, two or three substituents independently selected from halogen and C$_{1-6}$alkyl; R² is C$_{1-6}$alkyl; R³ is —C$_x$H$_{2x}$—; x is 1, 2, 3, 4, 5, 6 or 7.

Another embodiment of this invention is that compound of formula (Ia) can also be synthesized in analogy to Scheme 1 with racemic starting material and Scheme 2 without chiral separation step.

A detailed description of present invention of process steps is as following:

Step a) the formation of the isocyanate (III).

Isocyanate (III) is synthesized in the presence of a suitable base in a suitable solvent with phosgene reagent. The conversion as a rule is performed under a cooling condition.

The suitable solvent is selected from 2-MeTHF, THF, IPAc, EA, toluene and DCM, particularly the suitable solvent is DCM.

The suitable base is selected from Na$_2$CO$_3$, NaHCO$_3$, K$_2$CO$_3$, Na$_3$PO$_4$ and K$_3$PO$_4$. And particularly the base is aqueous Na$_2$CO$_3$ at concentration of 5-25 wt % or aqueous K$_2$CO$_3$ at concentration of 5-30 wt %. More particularly the base is aqueous Na$_2$CO$_3$ at concentration of 10-15 wt %. The addition rate of the base is controlled while the reaction temperature is between −20° C. and 40° C., particularly between 0° C. and 10° C.

The suitable phosgene reagent is selected from phosgene, diphosgene and triphosgene, particularly the phosgene reagent is triphosgene. The amount of triphosgene is 0.34-1.0 eq. of compound of formula (II), particularly 0.34-0.45 eq.

Step b) the formation of urea (V) via the addition reaction of isocyanate (III) and compound (IV).

The urea (V) is synthesized in a suitable organic solvent. The conversion as a rule is performed under a cooling condition The addition reaction is conducted in a suitable organic solvent, which is selected from 2-MeTHF, THF, IPAc, EA, toluene and DCM. Particularly the solvent is DCM.

The reaction is performed at temperature between 0° C. and 60° C., particularly between 5° C. and 25° C.

Step c) the formation of the compound of formula (VI) via the cyclization reaction of urea (V).

The compound of formula (VI) is synthesized via the cyclization of urea (V) in the presence of a suitable acid in a suitable organic solvent. The conversion as a rule is performed under a heating condition.

The suitable solvent is selected from 2-MeTHF, IPAc, EA, toluene, DCM, methanol and ethanol. Particularly the solvent is ethanol.

The suitable acid is selected from boron trifluoride etherate, phosphoric acid, sulphuric acid, HBr and HCl; particularly the acid is HCl, more particularly the acid is concentrated HCl. The addition rate of the acid is controlled while the reaction temperature is between 0° C. and 50° C., particularly between 25° C. and 50° C. while the releasing gas can be controlled. The reaction is performed at temperature between 25° C. and 78° C., particularly between 50° C. and 78° C.

Step d) the formation of the compound of formula (VII) by protection of the compound of formula (VI).

The compound of formula (VII) is synthesized in the presence of a suitable base with a suitable protecting reagent in a suitable solvent. The conversion as a rule is performed under a cooling condition.

The suitable protecting reagent is selected from the chloroformates and anhydrides. Particularly the protecting reagent is benzyl chloroformate or Boc anhyride, more particularly the protecting reagent is Boc anhyride.

The suitable solvent is selected from 2-MeTHF, THF, IPAc, EtOAc and DCM. Particularly the solvent is THF or 2-MeTHF.

The suitable base is selected from TEA, DIPEA, $Na_2CO_3$, $NaHCO_3$, $K_2CO_3$, $Na_3PO_4$ and $K_3PO_4$. Particularly the base is $Na_2CO_3$ or $NaHCO_3$, more particularly the base is aqueous $Na_2CO_3$ or aqueous $NaHCO_3$. The reaction is performed at a reaction temperature between 0° C. and 40° C., particularly between 0° C. and 5° C.

After an appropriate amount of time, usually 2-6 hours, the reaction is completed by monitoring with HPLC. The compound of formula (VII) is isolated by methods known to the skilled in the art such as by extraction. The crude the compound of formula (VII) is used directly for the next step.

Formation of the compound of formula (VII) can be achieved from direct cyclization of urea (V), which gives high conversion but causes partial racemization (4%-50% of R-isomer). The direct cyclization of urea (V) can be conducted in a solvent selected from DCM, ethanol, toluene and CPME with catalytic amount of base selected from sodium tert-butoxide, DBU, TMP, $Na_2CO_3$ and DMAP.

Step e) the formation of the compound of formula (VIII) via selective reduction of the compound of formula (VII).

The compound of formula (VIII) is synthesized in the presence of a suitable catalytic Lewis acid and a suitable reductive reagent in a suitable solvent. And the conversion as a rule is performed under a cooling condition.

The suitable solvent is selected from THF, 2-MeTHF and cyclopentyl methyl ether, particularly the solvent is THF or 2-MeTHF.

The suitable reductive reagent is selected from lithium aluminum hydride, sodium dihydro-bis-(2-methoxyethoxy) aluminate, borane dimethylsulfide, phenylsilane and borane tetrahydrofuran complex, particularly the reductive reagent is borane tetrahydrofuran complex.

And the amount of borane tetrahydrofuran complex is 1.6-5.0 eq. of the compound of formula (VII), particularly 1.6-2.0 eq.

The catalytic Lewis acid is selected from $InCl_3$, $YCl_3$, $ZnCl_2$, $Zn(OAc)_2$ and $BF_3.Et_2O$, particularly the Lewis acid is $BF_3.Et_2O$. And the amount of $BF_3.Et_2O$ is 0.05-1.1 eq. of the compound of formula (VII), particularly 0.2 eq.

The reaction is performed at a reaction temperature between −40 and 40° C., particularly between 10° C. and 15° C.

Usually 4-5 eq. of borane tetrahydrofuran complex can give 100% conversion but suffer from poor selectivity of reduction over other carbonyl groups. With catalytic amount of $BF_3.Et_2O$, not only the selectivity is improved but also the amount of borane tetrahydrofuran complex is decreased from 4-5 eq. to 1.6-2.0 eq.

Step f) the formation of the compound of formula (IX) via hydrolysis of the compound of formula (VIII).

The compound of formula (IX) is synthesized in the presence of a suitable base in a suitable solvent followed by a work-up procedure.

The suitable solvent is selected from THF, methanol and ethanol. Particularly the solvent is methanol.

The suitable base for hydrolysis is selected from LiOH, NaOH and KOH. Particularly the base is aq. NaOH.

The reaction is performed at temperature between 0° C. and 60° C., particularly between 25° C. and 40° C.

The compound of formula (IX) is isolated through a work-up procedure comprising extraction with a suitable organic solvent to remove the impurities and recrystallization in a suitable solvent.

The suitable organic solvent used in extraction is selected from THF, EA, IPAc, MTBE and toluene. Particularly the organic solvent used in extraction is IPAc.

The suitable solvent for recrystallization of the compound of formula (IX) is selected from IPAc, mixed solvent of methanol and water, mixed solvent of ethanol and water and mixed solvent of IPAc and heptane.

Step g) the formation of compound of formula (X) by de-protection of the compound of formula (IX).

Compound of formula (X) is synthesized in the presence of a suitable acid in a suitable solvent.

The suitable solvent is selected from DCM, dioxane, EtOAc, IPAc, IPA, acetone, MIBK and mixed solvent of MIBK and acetone. Particularly the solvent is MIBK.

The suitable acid is selected from TFA, phosphoric acid, MSA, sulphuric acid, HBr and HCl. Particularly the acid is TFA or HCl, and more particularly the acid is HCl.

The addition rate of the acid is controlled while the reaction temperature is maintained between 0° C. and 45° C., particularly between 8° C. and 25° C. while the releasing gas can be controlled.

The amount of acid is 3-10 eq. of the compound of formula (IX), particularly 3-4 eq.

After an appropriate amount of time, usually 0.5-2 hours, the reaction is completed with monitoring by HPLC. The compound of formula (X) is isolated as a solid through recrystallization in a suitable solvent.

The suitable solvent for recrystallization of compound of formula (X) is selected from acetonitrile, IPAc, MIBK, ethanol, acetone, mixed solvent of acetone and methanol, and mixed solvent of acetone and MIBK, particularly the solvent is acetone.

Step h) the formation of compound of formula (XIV) via Biginelli-like reaction.

Compound of formula (XIV) is synthesized in the presence of a suitable catalyst in a suitable solvent. And the conversion as a rule is performed under a heating condition.

This step is further optimized compared to prior art (CN101041658) by modifying each stage of Biginelli-like reaction, which is conducted as one-pot reaction via three stages as shown in Scheme 3: 1) the first stage is the formation of intermediate 1 through Knoevenagel condensation; 2) the second stage is the formation of intermediate 2; 3) the third stage is dehydration. The refined reaction condition greatly decreases the aromatization from 9.45% to <1% (impurity 1) and improves the yield from 70% to 84%.

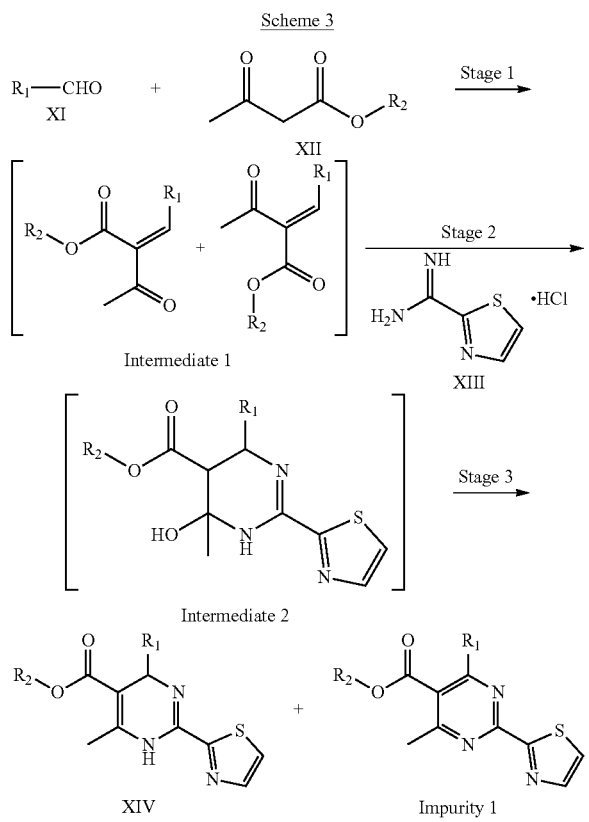

Scheme 3

The suitable solvent is selected from methanol, ethanol, IPA, tert-BuOH, 2,2,2-trifluroethanol and toluene, particularly the solvent is IPA.

The suitable catalyst used in the first stage of step h) is selected from TEA, a mixture of TEA and AcOH, pyridine, a mixture of pyridine and AcOH, glycine, β-alanine, GABA, a mixture of DBU and AcOH and a mixture of AcOH and piperidine, particularly the catalyst is a mixture of AcOH and piperidine. The first stage is performed at the temperature between 0° C. and 50° C., particularly at the temperature between 25° C. and 30° C.

The suitable base used in the second stage of step h) is selected from TEA, DIPEA, DBU, sodium ethoxide and sodium tert-butoxide, particularly the base is sodium ethoxide or TEA. To decrease the impurity formation, the addition sequence is defined as that compound (XIII) is added first followed by the addition of base with controlled addition rate. The second stage is performed at the temperature between 25° C. and 80° C., particularly between 25° C. and 30° C.

The third stage of step h) is performed at the temperature between 50° C. and 80° C., particularly at the temperature between 70° C. and 75° C.

Step i) the formation and recrystallization of the enantiomeric salt of compound of formula (XVI) or solvate.

The enantiomeric salt of compound of formula (XVI) is synthesized in the presence of a suitable organic acid in a suitable organic solvent. The conversion as a rule is performed under a heating condition.

The suitable organic acid used in enantiomeric salt formation is selected from D-(+)-DTTA, L-DTTA, L-Tartaric acid, D-DBTA, (+)-CSA, (S)-(+)-1,1'-Binaphthyl-2,2'-diyl hydrogen phosphate and (R)-(−)-1,1'-Binaphthyl-2,2'-diyl hydrogen phosphate, particularly the organic acid is (R)-(−)-1,1'-Binaphthyl-2,2'-diyl hydrogen phosphate.

The suitable organic solvent used in enantiomeric salt formation is selected from THF, MTBE, CPME, MeOH, EtOH, IPA, IPAc, EA, MEK, DCM, heptane, acetone, ACN, toluene, MIBK, trifluoroethanol and mixed solvent of ACN and MTBE, mixed solvent of ACN and IPAc, mixed solvent of ACN/EA, mixed solvent of ACN/ethanol, mixed solvent of MIBK and water and mixed solvent of ethanol and water, particularly the organic solvent is ethanol. The crude enantiomeric salt of compound of formula (XVI) or solvate is isolated as solid, and the other enantiomeric salt as a rule remained in the mother liquor.

The suitable amount of organic acid (XV) is 0.5-1.0 eq. of compound of formula (XIV), particularly 0.85 eq-1.0 eq.

The enantiomeric salt formation as a rule is performed at the temperature between 25° C. and 80° C., particularly at the temperature between 70° C. and 80° C.

To further improve the chiral purity, recrystallization of the crude enantiomeric salt of compound of formula (XVI) or solvate is achieved in a suitable solvent. The suitable solvent used in recrystallization is selected from ethanol, MIBK, IPAc, toluene and MTBE, particularly the solvent is ethanol.

Step j) the recovery of enantiomeric compound of formula (XVII) from its enantiomeric salt of formula (XVI) or solvate.

Compound of formula (XVII) is recovered from its enantiomeric salt of formula (XVI) or solvate in the presence of a suitable base in a suitable organic solvent, followed by a suitable work-up procedure.

The suitable base is selected from TEA, DIPEA, methyldicyclohexylamine, NMM, NaOH, $Na_2CO_3$, $NaHC_3$, KOH and sodium tert-butoxide, particularly the base is NaOH. The suitable amount of base is 1.0-2.0 eq. of enantiomeric salt of formula (XVI), particularly 1.1 eq.

The reaction is performed in an organic solvent selected from DCM, 2-MeTHF, MTBE and fluorobenzene, particularly the organic solvent is DCM.

The removal of water in this step can decrease the formation of impurities in step k). The suitable work-up procedure used to remove the water is selected from drying over molecular sieve, Na₂SO₄ or MgSO₄ and azeotropic removal of water, particularly the work-up procedure is azeotropic removal of water.

Step k) the formation of compound of formula (XVIII) via the bromination reaction of compound of formula (XVII).

Compound of formula (XVIII) is synthesized in the presence of a suitable bromination reagent with or without a suitable additive in a suitable organic solvent. And the conversion as a rule is performed under a heating condition.

The suitable bromination reagent is selected from NBS, bromine, pyridine tribromide and 1,3-dibromo-5,5-dimethylhydantion, particularly the bromination reagent is NBS. The bromination reaction is performed at the temperature between 0° C. and 80° C., particularly between 35° C. and 40° C.

The suitable additive is selected from AcCl, trimethyl orthoformate, triethyl orthoformate, trifluoroacetic anhydride, acetic anhydride and PBr₃, particularly the additive is PBr₃.

The reaction is usually performed in an organic solvent selected from carbon tetrachloride, 1,2-Dichloroethane, ACN, acetic acid, fluorobenzene, chlorobenzene and DCM, particularly the organic solvent is DCM.

Step l) the formation of compound of formula (I) via the substitution reaction of compound of formula (XVIII) with compound of formula (X).

Compound of formula (I) is synthesized in the presence of a suitable base in a suitable organic solvent.

The suitable base is selected from TMP, DIPEA, TEA, tripropylamine, N,N-dicyclohexylmethylamine, DBU, NMM, 2,6-lutidine, 1-methylimidazole, 1,2-dimethylimidazole, tetra methylpiperidine-4-ol, Na₂CO₃, K₂CO₃, NaHCO₃ and tris(2-hydroxylethyl)amine; particularly the base is TMP or tris(2-hydroxylethyl)amine; and more particularly the base is tris(2-hydroxylethyl)amine.

The suitable pKa and nucleophilicity of the base are directly related to the yield and impurities formation in this step. Both TMP and tris(2-hydroxylethyl)amine could result in good yield with high selectivity, but hydrazine related impurities might be introduced to the final API when using TMP as the base.

The suitable organic solvent is selected from THF, IPAc EtOAc, MTBE, fluorobenzene, chlorobenzene and DCM, particularly the organic solvent is DCM.

The substitution reaction as a rule is performed at the temperature between 0° C. and 40° C., particularly at temperature between 10° C. and 25° C.

All the impurities in the last three steps (step j), step k) and step l)) are brought to the final crude product of compound of formula (I). An efficient purification procedure through an acid-base work-up and recrystallization is successfully developed to ensure the purity of API.

The purification procedure of compound of formula (I) includes: 1) acid-base work-up with a suitable acid and a suitable base in a suitable solvent; and 2) recrystallization which is performed with or without suitable seeding in a suitable organic solvent.

The acid used in the acid-base work-up for purification of compound of formula (I) is selected from HCl, HBr, H₂SO₄, H₃PO₄, MSA, toluene sulfonic acid and camphor sulfonic acid, particularly the acid is H₃PO₄. The concentration of aqueous H₃PO₄ is selected from 15 wt % to 60 wt %; particularly the concentration of aqueous H₃PO₄ is from 35 wt % to 40 wt %. And the amount of H₃PO₄ is 5-25 eq. of compound of formula (XVII), particularly 10-15 eq. The amount of H₃PO₄ is essential and carefully designed to get the maximum recovery of API and minimum impurities.

The base used in the acid-base work-up for purification of compound of formula (I) is selected from NaOH, KOH, K₂CO₃ and Na₂CO₃, particularly the base is NaOH.

The suitable organic solvent used for extracting impurities in the acid-base work-up for purification of compound of formula (I) is selected from MTBE, EA, IPAc, butyl acetate, toluene and DCM; particularly, the organic solvent is EA or DCM; and more particularly the solvent is DCM.

The suitable solvent for recrystallization of compound of formula (I) is selected from IPA, ethanol, EtOAc, IPAc, butyl acetate, toluene, MIBK, mixed solvent of acetone and water, mixed solvent of IPA and water, and mixed solvent of ethanol and water; particularly the solvent is mixed solvent of ethanol and water. Seeding amount is 0.5-5 wt % of compound of formula (I), particularly the seeding amount is 1 wt %.

EXAMPLES

Example 1

Preparation of ethyl 3-isocyanato-2,2-dimethyl-propanoate (Example 1)

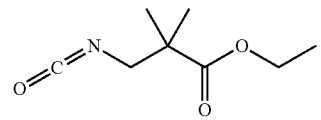

The title compound was prepared according to following scheme:

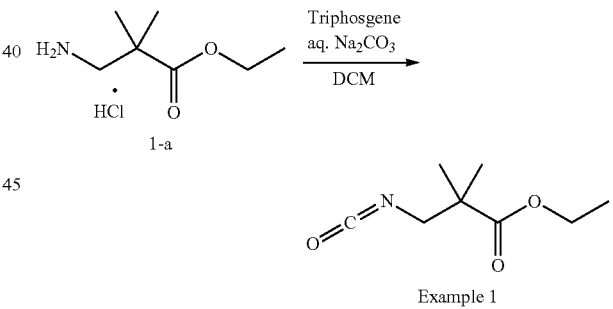

A 100 L glass-lined reactor was charged with ethyl 3-amino-2,2-dimethyl-propanoate hydrochloride (2.40 kg, 13.21 mol, Compound1-a) and DCM (28.8 L) at 20° C.-25° C. To the reaction mixture, cooled to 0° C.-5° C., triphosgene (1.76 kg, 5.93 mol) was added in portions. Then aqueous Na₂CO₃ (10 wt %, 2.80 kg, 26.4 mol) was added while the temperature was maintained below 8° C. The reaction mixture was stirred at 5° C.-8° C. for another 2 hours. Then to the resulting reaction mixture was washed with brine (20 wt %, 12.0 L) and aqueous Na₂CO₃ (20 wt %, 12.0 L), then the organic phase was filtered through a pad of Na₂SO₄ and the filtrate was used directly for the next step without further purification. Analytically pure Example 1 was obtained as an oil by direct concentration of the crude solution. ¹H NMR (400 MHz, CDCl₃) δ 4.20 (d, J=8.0, 2H), 3.42 (s, 2H), 1.30 (t, J=8.0, 3H), 1.25 (s, 6H)

Example 2

Preparation of O1-tert-butyl O3-methyl (3S)-4-[(3-ethoxy-2,2-dimethyl-3-oxo-propyl)carbamoyl]piperazine-1,3-dicarboxylate (Example 2)

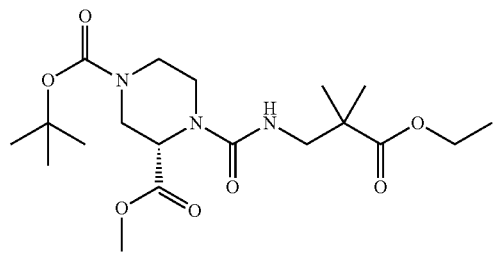 [SMILES: CCOC(=O)C(C)(C)CNC(=O)N1CCN(C(=O)OC(C)(C)C)C[C@H]1C(=O)OC]

The title compound was prepared according to following scheme:

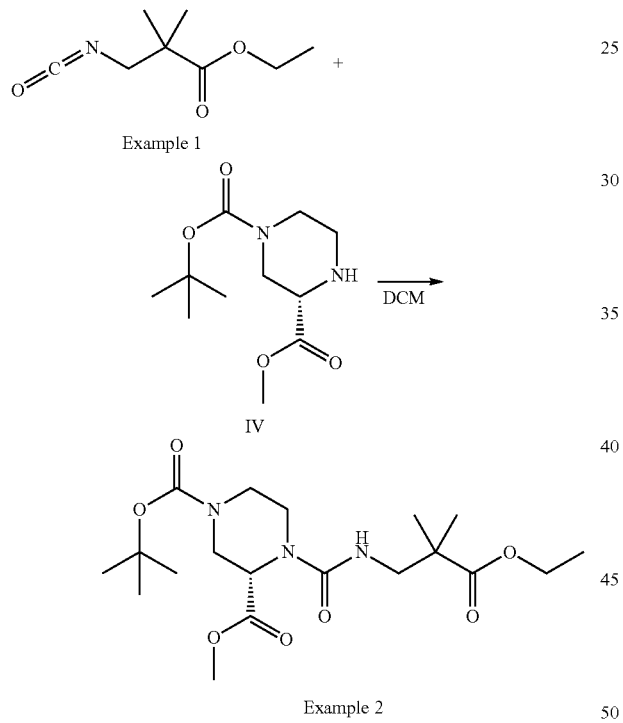

A 50 L glass-lined reactor was charged with the above solution of ethyl 3-isocyanato-2,2-dimethyl-propanoate (Example 1) in DCM. To the solution, cooled to 5-10° C., was added O1-tert-butyl O3-methyl (3S)-piperazine-1,3-dicarboxylate (2.64 kg, 10.81 mol, Compound IV) in portions below 10° C. The reaction mixture was stirred for 2 hours at 25° C. The solvent was removed at 40° C./0.07 MPa to give the crude Example 2 (4.9 kg, purity: 94.98%) which was used directly for the next step. Analytically pure Example 2 was obtained as an oil by flash chromatography. $^1$H NMR (400 MHz, CDCl$_3$) δ 5.45-5.48 (m, 1H), 4.85 (s, br, 1H), 4.54 (d, J=13.6, 1H), 4.12 (q, J=7.6, 2H), 3.69 (s, 3H), 3.30-3.38 (m, 4H), 3.06-3.09 (m, 1H), 2.87 (s, br, 1H), 1.41 (s, 9H), 1.24 (t, J=7.6, 3H), 1.16 (s, 6H); MS m/e=416.1 [M+H]$^+$.

Example 3

Preparation of ethyl 3-[(8aS)-1,3-dioxo-6,7,8,8a-tetrahydro-5H-imidazo[1,5-a]pyrazin-2-yl]-2,2-dimethyl-propanoate hydrochloride (Example 3)

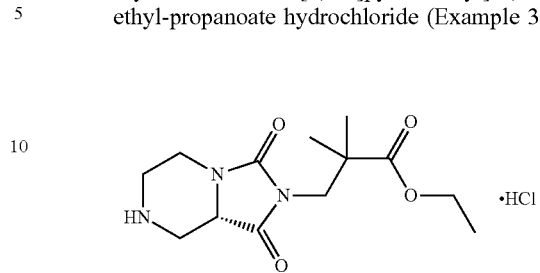

The title compound was prepared according to following scheme:

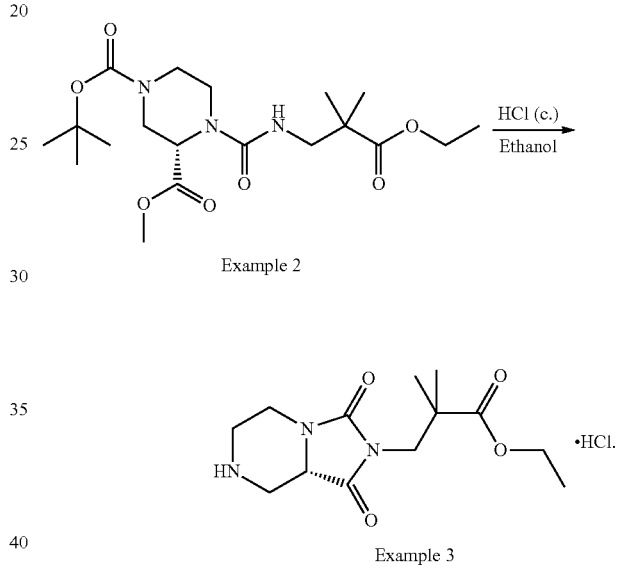

A 50 L glass-lined reactor was charged with O1-tert-butyl O3-methyl (3S)-4-[(3-ethoxy-2,2-dimethyl-3-oxo-propyl)carbamoyl]piperazine-1,3-dicarboxylate (4.9 kg, crude Example 2 from last step) and ethanol (24.5 L). To the reaction mixture was added concentrated HCl (2.95 L) slowly while maintaining the temperature between 15° C. and 45° C. Then the reaction mixture was stirred at 70° C.-80° C. for 5 hours. To the resulting mixture, cooled to 40° C., was added toluene (14.7 L). The water was removed by azeotropic removal with toluene and ethanol at 55° C./0.1 MPa until the solid was observed. The residual was cooled to 15° C.-20° C. and stirred for another 0.5 hour. The solid was collected by centrifugal separation and 2.40 kg of the product Example 3 was obtained after drying. The filtrate was concentrated to about 3.50 L. Additional 670 g of the product Example 3 was obtained after filtration and drying. (purity: 97.2%, yield for two steps: 89%) $^1$H NMR (400 MHz, DMSO-d$^6$) δ 9.94 (s, 1H), 4.55-4.85 (m, 1H), 3.99-4.06 (m, 3H), 3.49-3.54 (m, 3H), 3.31-3.47 (m, 2H), 3.06-3.12 (m, 1H), 2.85-2.88 (m, 1H), 1.18 (t, J=7.2, 3H), 1.10 (s, 6H); MS m/e=284.1 [M+H]$^+$.

Example 4

Preparation of tert-butyl (8aS)-2-(3-ethoxy-2,2-dimethyl-3-oxo-propyl)-1,3-dioxo-5,6,8,8a-tetrahydroimidazo[1,5-a]pyrazine-7-carboxylate (Example 4)

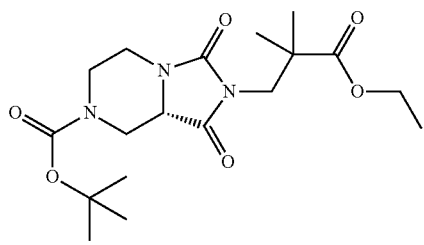 [SMILES: CCOC(=O)C(C)(C)CN1C(=O)[C@@H]2CN(C(=O)OC(C)(C)C)CCN2C1=O]

The title compound was prepared according to following scheme:

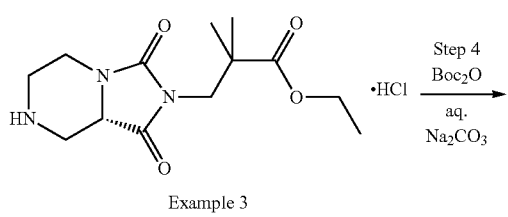

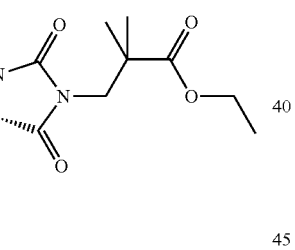

Example 4

A 50 L glass-lined reactor was charged with ethyl 3-[(8aS)-1,3-dioxo-6,7,8,8a-tetrahydro-5H-imidazo[1,5-a]pyrazin-2-yl]-2,2-dimethyl-propanoate hydrochloride (3.07 kg, 9.6 mol, Example 3) and THF (11.7 L). To the mixture, cooled to 0-5° C., was added Boc₂O (560 g, 9.79 mol) and followed with adding aqueous Na₂CO₃ (10 wt %, 5.6 kg, 5.28 mol) slowly at 4° C.-8° C. The reaction mixture was stirred for another 4 hours at 5° C.-10'° C. To the resulting mixture was added toluene (7.98 L). After stirring for 0.5 hour, the phases were separated. The organic layer was washed with 20% brine (7.98 L) and then dried over Na₂SO₄. The organic phase was concentrated at 40° C. to give the crude product Example 4 (3.34 kg, purity (UV 215): 99.1%) as oil which was used directly for the next step. ¹H NMR (400 MHz, DMSO-d⁶) δ ¹H NMR (400 MHz, DMSO-d⁶) δ 4.16-4.20 (m, 2H), 4.01 (t, J=7.2, 2H), 3.85-3.89 (m, 2H), 3.50 (s, 2H), 2.91-2.97 (m, 1H), 2.80 (br, 2H), 1.61 (s, 9H), 1.26 (t, J=7.2, 3H), 1.19 (s, 6H); MS m/e=328.1 [M+H]⁺.

Example 5

Preparation of tert-butyl (8aR)-2-(3-ethoxy-2,2-dimethyl-3-oxo-propyl)-3-oxo-5,6,8,8a-tetrahydro-1H-imidazo[1,5-a]pyrazine-7-carboxylate (Example 5)

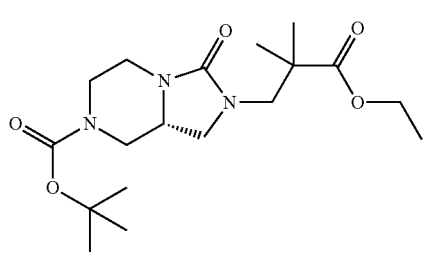 [SMILES: CCOC(=O)C(C)(C)CN1C[C@@H]2CN(C(=O)OC(C)(C)C)CCN2C1=O]

The title compound was prepared according to following scheme:

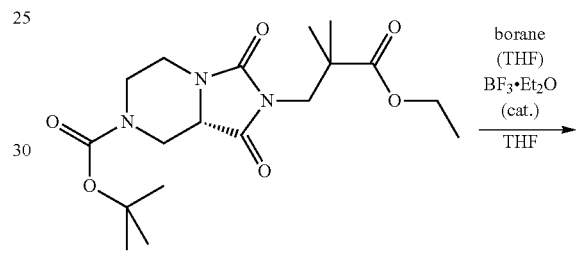

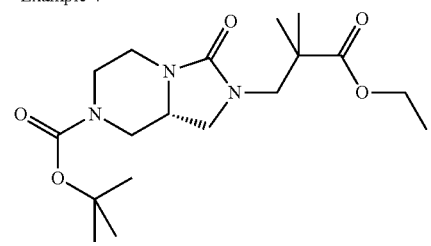

Example 5

A 50 L glass-lined reactor was charged with tert-butyl (8aS)-2-(3-ethoxy-2,2-dimethyl-3-oxo-propyl)-1,3-dioxo-5,6,8,8a-tetrahydroimidazo[1,5-a]pyrazine-7-carboxylate (3.33 kg, 8.50 mol, Example 4) and THF (6.51 L). The suspension was degassed under vacuum and purged with N₂ for three times. To the solution, cooled to 0° C.-5° C., was added BF₃.Et₂O (241 g, 1.70 mol) and followed by adding borane tetrahydrofuran complex (1 M, 17 L, 2.0 eq.) at 5° C.-10° C. over 3.5 hours. After addition, the reaction mixture was stirred at 10° C. for another 18 hours followed by adding EtOAc (7.49 L) and then aqueous Na₂CO₃ (3 wt %, 24.0 kg) over 3-4 hours below 10° C. Then the reaction mixture was stirred at 5° C.-10° C. for 1 hour. After removal of the solid, the phases of the filtrate were separated and the aqueous layer was extracted with EA (7.49 L). The combined organic layer was washed with brine (20 wt %, 5.51 L) and then concentrated at 40° C. to give the crude product Example 5 (3.04 kg, purity (UV 215): 75.5%) as yellow oil which was used directly for the next step. MS m/e=370.1 [M+H]⁺.

Example 6

Preparation of 3-[(8aR)-7-tert-butoxycarbonyl-3-oxo-5,6,8,8a-tetrahydro-1H-imidazo[1,5-a]pyrazin-2-yl]-2,2-dimethyl-propanoic acid (Example 6)

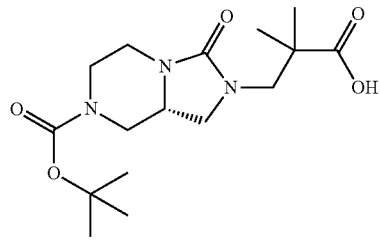 [SMILES: CC(C)(C)OC(=O)N1CCN2C(=O)N(CC(C)(C)C(=O)O)C[C@@H]2C1]

The title compound was prepared according to following scheme:

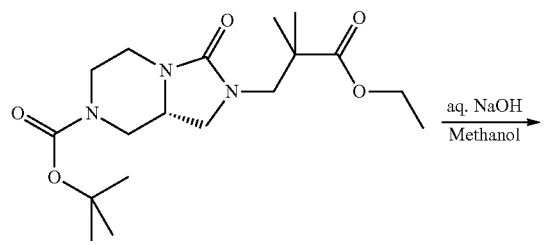

A 20 L three-necked round-bottomed flask equipped with mechanical stirrer, thermometer and nitrogen bubbler was charged with tert-butyl (8aS)-2-(3-ethoxy-2,2-dimethyl-3-oxo-propyl)-1,3-dioxo-5,6,8,8a-tetrahydroimidazo[1,5-a]pyrazine-7-carboxylate (80 wt %, 3.03 kg, 6.56 mol, Example 5) and methanol (3.12 L) at 15° C.-20°. To the reaction mixture, cooled to 0° C.-5° C., was added aq. NaOH (10 wt %, 5.25 kg, 13.12 mol) slowly at 4° C.-10° C. After addition, the reaction mixture was stirred at 20° C.-25° C. for another 16 hours, and then diluted with water (3.64 L). Methanol was removed under vacuum 40° C./0.09-0.1 MPa. The resulting residual was extracted with IPAC (4.85 L) twice. The aqueous layer, cooled to 5-10° C., was adjusted to pH=3.0-4.0 with aq. HCl (6 M, 1.90 L) blow 10° C. and then solid formed. The suspension was stirred at 5-10° C. for 1 hour. The solid was collected by filtration and washed with water, then dried at 45-50° C. in vacuo (0.09-0.1 MPa) for 16 hours to afford the product Example 6 (2.12 kg, purity (UV 215): 99.2%, chiral purity: 99.2%, yield for three steps: 65%) as a white solid. $^1$H NMR (400 MHz, CDCl$_3$)$^1$H NMR (400 MHz, CDCl$_3$) δ 3.98-4.09 (m, 2H), 3.76-3.80 (m, 1H), 3.47-3.52 (m, 2H), 3.30-3.41 (m, 2H), 3.00-3.04 (s, 1H), 2.85-2.88 (m, 1H), 2.60-2.75 (m, 2H), 1.45 (s, 9H), 1.22 (s, 6H); MS m/e=342.1 [M+H]$^+$.

Example 7

Preparation of 3-[(8aS)-3-oxo-1,5,6,7,8,8a-hexahydroimidazo[1,5-a]pyrazin-2-yl]-2,2-dimethyl-propanoic acid hydrochloride (Example 7)

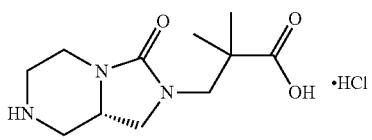 [SMILES: CC(C)(CN1C[C@@H]2CNCCN2C1=O)C(=O)O ; Cl]

The title compound was prepared according to following scheme:

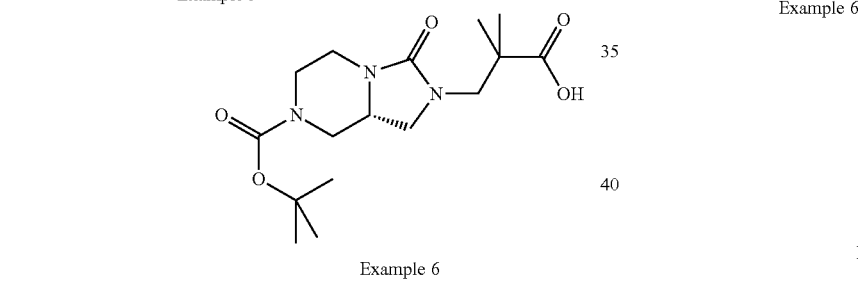

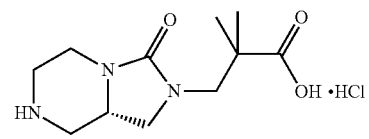

A 20 L three-necked round-bottomed reactor equipped with mechanical stirrer, thermometer and nitrogen bubbler was charged with 3-[(8aR)-7-tert-butoxycarbonyl-3-oxo-5,6,8,8a-tetrahydro-1H-imidazo[1,5-a]pyrazin-2-yl]-2,2-dimethyl-propanoic acid (2.10 kg, 6.15 mol, Example 6) followed by addition of MIBK (8.82 L) at 15° C.-20° C. To the suspension was added slowly HCl (12 M, 1.54 L) at 15° C.-27° C. The reaction mixture was stirred for 1 hour. The reaction mixture was concentrated in vacuo at 45° C. (0.09-0.1 MPa) to afford a pink oil. To the residue was added acetone (2.2 L) and the suspension was stirred at 18° C.-23° C. for 16 hours. The salt was collected by filtration using a Büchner funnel and washed with acetone. The wet cake was dried in a vacuum oven (40° C./Ca. 0.1 MPa) with a nitrogen bleed for 16 hours to afford Example 7 (1.43 kg, purity: 100%, chiral purity: 100%, yield: 83.7%) as white solid. $^1$H NMR (400 MHz, DMSO-d$^6$) δ 12.42 (br, 1H), 9.75 (br, 2H), 3.91-3.97 (m, 1H), 3.70-3.75 (m, 1H), 3.12-3.29 (m, 5H), 3.01-3.04 (m, 1H), 2.65-2.75 (m, 2H), 1.24 (s, 6H); MS m/e=242.1 [M+H]$^+$.

Example 8

Preparation of ethyl 4-(3-fluoro-2-methyl-phenyl)-6-methyl-2-thiazol-2-yl-1,4-dihydropyrimidine-5-carboxylate (Example 8)

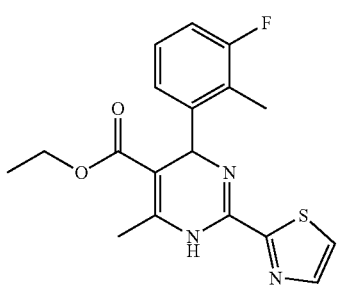 [SMILES: CCOC(=O)C1=C(C)NC(c2nccs2)=NC1c1cccc(F)c1C]

The title compound was prepared according to following scheme:

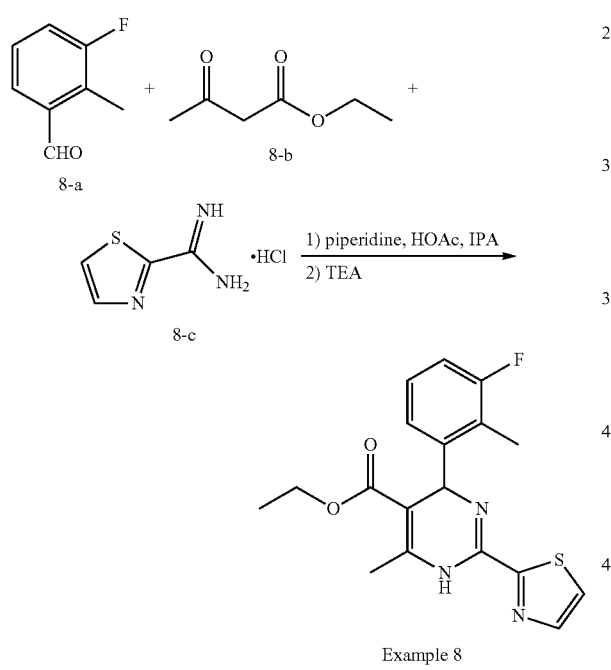

A 1500 L reactor equipped with mechanical stirrer, thermometer and nitrogen bubbler was charged with 3-fluoro-2-methyl-benzaldehyde (32.68 kg, 23.66 mol, compound 8-a), IPA (256.5 kg) and ethyl 3-oxobutanoate (30.78 kg, 23.65 mol, compound 8-b) at 20° C.-30° C. To the reaction mixture was added piperidine (2.03 kg) and acetic acid (1.58 kg) at 20° C.-30° C. After 4 hours, to the resulting solution was added thiazole-2-carboxamidine hydrochloride (36.51 kg, 90 wt %, 20.11 mol, compound 8-c) followed by addition of triethylamine (23.90 kg, 23.66 mol) over 50 mins. The reaction mixture was stirred at 25° C.-30° C. for another 12 hours and then stirred at 70° C.-75° C. for 8 hours. After the reaction was finished, the reaction mixture was cooled to 30° C. and water (261 kg) was added over 50 mins. The suspension was stirred at 20° C.-30° C. for another 10 hours. The solid was collected by filtration and washed with IPA/water (v/v=1:1, 33 L) and water (33 L). The wet cake was dried in a vacuum oven (50° C./Ca. 0.1 MPa) with a nitrogen bleed for 16 hours to afford the product Example 8 (61 kg, purity: 99.5%, yield: 83.9%) as a yellow solid. $^1$H NMR (400 MHz, DMSO-d$^6$) δ 9.86 (s, 1H), 7.96 (d, J=3.2 Hz, 1H), 7.88 (d, J=3.2 Hz, 1H), 7.15-7.20 (m, 1H), 6.99-7.04 (m, 1H), 5.83 (s, 1H), 3.94 (q, J=7.2 Hz, 2H), 2.48 (s, 3H), 2.44 (d, J=1.6 Hz, 3H), 1.09 (t, J=7.2 Hz, 3H); MS m/e=360.0 [M+H]$^+$.

Example 9

Preparation of ethyl (4S)-4-(3-fluoro-2-methyl-phenyl)-6-methyl-2-thiazol-2-yl-1,4-dihydropyrimidine-5-carboxylate mono (R)-(−)-1,1'-Binaphthyl-2,2'-diyl hydrogenphosphate salt (Example 9)

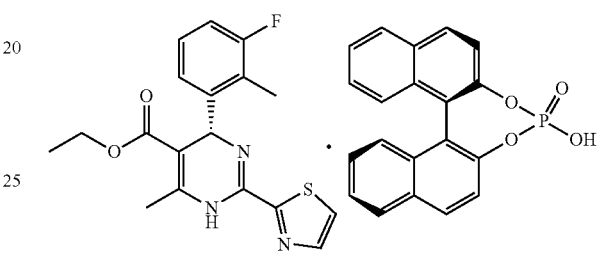

The title compound was prepared according to following scheme:

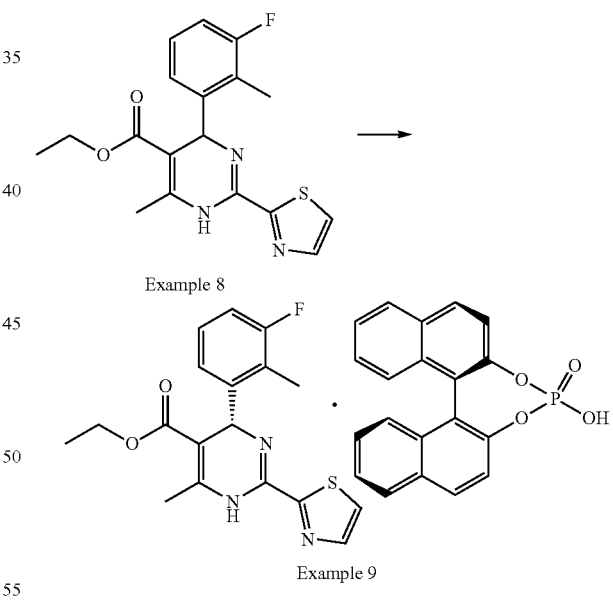

A 1500 L reactor equipped with mechanical stirrer, thermometer and nitrogen bubbler was charged with 4-(3-fluoro-2-methyl-phenyl)-6-methyl-2-thiazol-2-yl-1,4-dihydropyrimidine-5-carboxylate (61 kg, 169.7 mol, Example 8) and ethanol (481 kg) at 20-30° C. The reaction mixture was heated to 75° C. and stirred at 75° C. until all yellow solid was dissolved. (R)-(−)-1,1'-Binaphthyl-2,2'-diyl hydrogen phosphate (59.2 kg, 170.0 mol) was added and the agitation was maintained for 4 hours. The reaction mixture was slowly cooled to 30° C. in 4 hours, and then filtered. The collected solid was washed with ethanol (60 L) and then charged back to a 1500 L reactor. DCM (600 L) was added and the suspension was heated to reflux. To the suspension was added ethanol (300 L) over 0.5 hour and the agitation was maintained for 0.5 hour. Additional 300 L of ethanol was added over 0.5 hour at 40° C. DCM was distilled off at 38-60° C., the resulting mixture was stirred at 60° C. for another hour and then cooled from 60° C. to 30° C. over 8 hours. The chiral salt was collected by centrifuge and washed with ethanol (60 L). The wet cake was dried in a vacuum oven (50° C./Ca. 0.1 Mpa) with a nitrogen bleed for 24 hours to afford Example 9 (52.7 kg, purity: 99.6%, chiral purity: 99.1%, yield: 44%) as a light-yellow solid. $^1$H NMR (400 MHz, DMSO-d$^6$) δ 8.14 (d, J=8.8 Hz, 2H), 8.04-8.08 (m, 4H), 7.48-7.54 (m, 4H), 7.33-7.37 (m, 2H), 7.19-7.25 (m, 3H), 7.05-7.25 (m, 2H), 5.87 (s, 1H), 3.99 (q, J=7.2 Hz, 2H), 2.46 (s, 3H), 2.44 (s, 3H), 1.04 (t, J=7.2 Hz, 3H); MS m/e=360.0 [M+H]$^+$. The absolute structure was confirmed by XRPD.

Example 10

Preparation of 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Example 10)

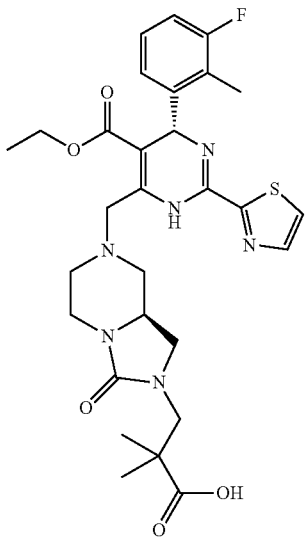 [SMILES: CCOC(=O)C1=C(CN2CCN3C(=O)N(CC(C)(C)C(=O)O)C[C@@H]3C2)NC(c2nccs2)=N[C@H]1c1cccc(F)c1C]

The title compound was prepared according to following scheme:

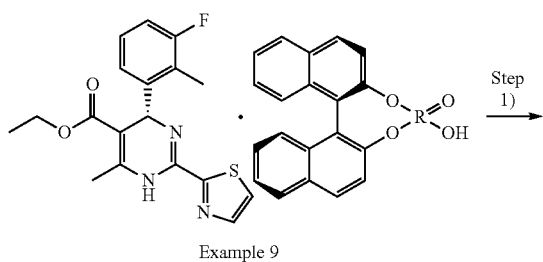

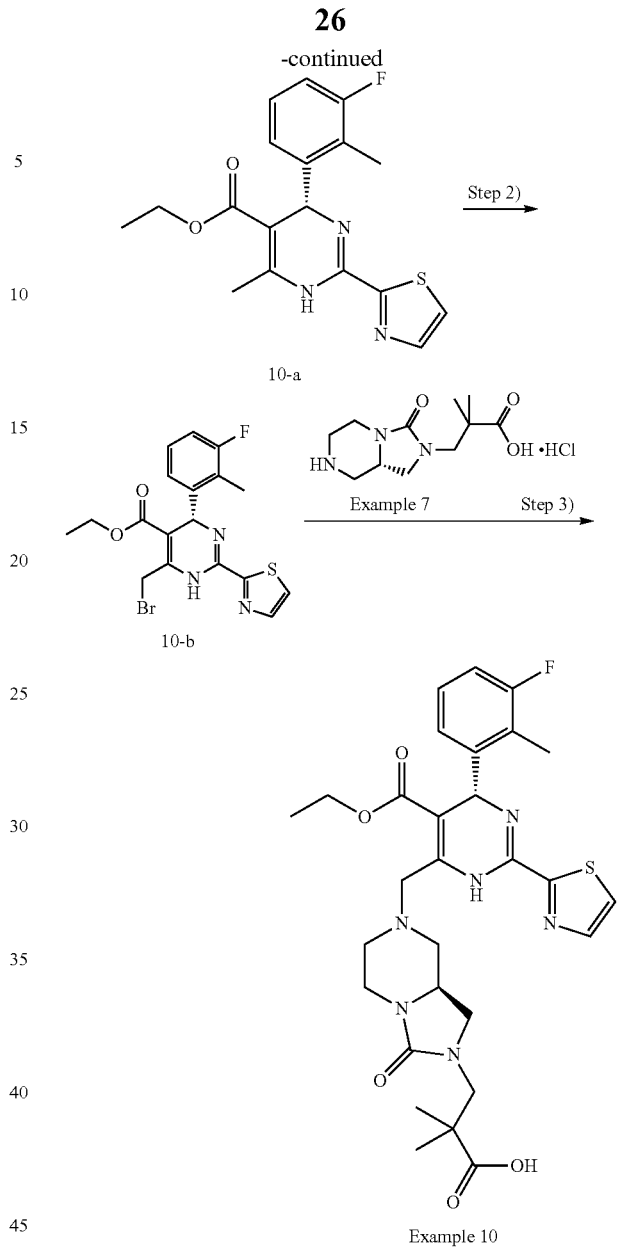

Step 1) Preparation of ethyl (4S)-4-(3-fluoro-2-methyl-phenyl)-6-methyl-2-thiazol-2-yl-1,4-dihydropyrimidine-5-carboxylate (Compound 10-a)

A 10 L flask equipped with mechanical stirrer, thermometer and nitrogen bubbler was charged with ethyl (4S)-4-(3-fluoro-2-methyl-phenyl)-6-methyl-2-thiazol-2-yl-1,4-dihydropyrimidine-5-carboxylate mono (R)-(−)-1,1'-Binaphthyl-2,2'-diyl hydrogenphosphate salt (500.0 g, 706 mmol, Example 9) and DCM (5.0 L). To the suspension was added aqueous NaOH (20 wt %, 1.1 eq., 155.4 g, 777 mmol) dropwise over 10 min at 20° C.-30° C. The reaction mixture was stirred at 20-30° C. for 4 hours. Then the resulting reaction mixture was filtered and the collected solid was washed with DCM (500 mL). The combined filtrate was washed with water (1.0 L) and concentrated till dryness in vacuo. To the residue was added fresh DCM (1.0 L), the resulting solution was concentrated till dryness in vacuo and this process was repeated twice. The resulting yellow oil (compound 10-a) was dissolved in DCM (2.5 L) and used in the next step without further purification.

Step 2) Preparation of ethyl (4S)-6-(bromomethyl)-4-(3-fluoro-2-methyl-phenyl)-2-thiazol-2-yl-1,4-dihydropyrimidine-5-carboxylate (Compound 10-b)

A 10 L flask equipped with mechanical stirrer, thermometer and nitrogen bubbler was charged with a solution of ethyl (4S)-4-(3-fluoro-2-methyl-phenyl)-6-methyl-2-thiazol-2-yl-1,4-dihydropyrimidine-5-carboxylate (706 mmol, compound 10-a) in DCM (4.0 L) from step 1). To the reaction mixture, heated to 32° C.-37° C., was added $PBr_3$ (2.71 g, 7.06 mmol) and followed by addition of NBS (125.6 g, 706 mmol) in portions while maintaining the temperature at 35° C.-40° C. After 0.5 hour, additional batch of NBS (12.6 g, 70.6 mmol) was added to reaction mixture which was carefully monitored by HPLC until the conversion >95%. The resulting solution of compound 10-b was cooled to 10-20° C. and used directly for the next step. MS m/e=436.1/438.0 [M+H]$^+$.

Step 3) preparation of 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Example 10)

A 10 L flask equipped with mechanical stirrer, thermometer and nitrogen bubbler was charged a solution of ethyl (4S)-6-(bromomethyl)-4-(3-fluoro-2-methyl-phenyl)-2-thiazol-2-yl-1,4-dihydropyrimidine-5-carboxylate in DCM from the last step. To the reaction mixture, cooled to 10-20° C., was added 3-[(8aS)-3-oxo-1,5,6,7,8,8a-hexahydroimidazo[1,5-a]pyrazin-2-yl]-2,2-dimethyl-propanoic acid hydrochloride (193 g, 635 mmol, purity: 91.6 wt %, Example 7) and followed by addition of triethanolamine (329 g, 2.33 mol) in DCM (350 mL) in portions below 25° C. The reaction mixture was stirred at 20° C.-30° C. for 16 hours. Then to the resulting reaction mixture was added water (1.25 L) and aqueous layer was adjusted to pH=3-4 using $H_3PO_4$ (85 wt %). After phase separation, the organic phase was washed with acidic water (1.25 L, $H_3PO_4$ solution with pH=2-3). After phase separation, the organic phase was extracted with aqueous $H_3PO_4$ solution (35 wt %, 1980 g) once and aqueous $H_3PO_4$ solution (35 wt %, 990 g) once. The combined aqueous layer was extracted with DCM (500 mL). To the aqueous layer, cooled to 0° C.-10° C., was added DCM (2.0 L). Then the aqueous layer was adjusted to pH=3-4 with aqueous NaOH solution (50 wt %, 770 g). After phase separation, the organic phase was washed with water (1.5 L) and filtered through celite (25 g) and then concentrated to about 500 mL in vacuo. The residue was diluted with ethanol (500 mL) and concentrated to about 500 mL in vacuo and this process was repeated one more time. Then the residue was diluted again with ethanol (1700 mL) and heated to 70-80° C. till all solid was dissolved. Water (2.20 L) was added to previous solution via an addition funnel while maintaining inner temperature between 60° C. and 78° C. Then the reaction mixture was cooled to 55° C. over 2 hours and maintained at 50° C.-55° C. for 1 hour, then cooled to 25° C. over 3 hours and stirred at 25° C. for another hour. The solid was collected by filtration and washed with ethanol/water (v/v=1/1, 250 g). The wet cake was dried in a vacuum oven (45° C.-55° C./Ca. 0.1 Mpa with a nitrogen bleed) for 35 hours to afford the product Example 10 (260.0 g, purity: 99.1%, chiral purity: 99.8%, yield: 61.5%) as a light-yellow solid. $^1$H NMR (400 MHz, DMSO-d$^6$) δ 12.35 (s, 1H), 9.60 (s, 1H), 8.01 (d, J=3.2 Hz, 2H), 7.93 (d, J=3.2 Hz, 2H), 7.15-7.19 (m, 1H), 7.01-7.05 (m, 2H), 5.89 (s, 1H), 3.87-4.00 (m, 4H), 3.62-3.73 (m, 2H), 3.33-3.39 (m, 1H), 3.27 (d, J=14.0 Hz, 1H), 3.16 (d, J=14.0 Hz, 1H), 2.93-3.00 (m, 2H), 2.77-2.82 (m, 2H), 2.45 (t, J=1.6 Hz, 3H), 2.15 (d, J=11.2 Hz, 1H), 2.02 (d, J=11.2 Hz, 1H), 1.03-1.08 (m, 9H); MS m/e=599.6 [M+H]$^+$.

Example 11

Preparation of 4-(2-chloro-4-fluoro-phenyl)-6-methyl-2-thiazol-2-yl-1,4-dihydropyrimidine-5-carboxylic acid methyl ester (Example 11)

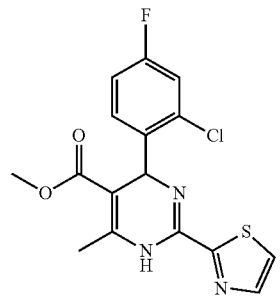 [SMILES: COC(=O)C1=C(C)NC(c2nccs2)=NC1c1ccc(F)cc1Cl]

The title compound was prepared according to following scheme:

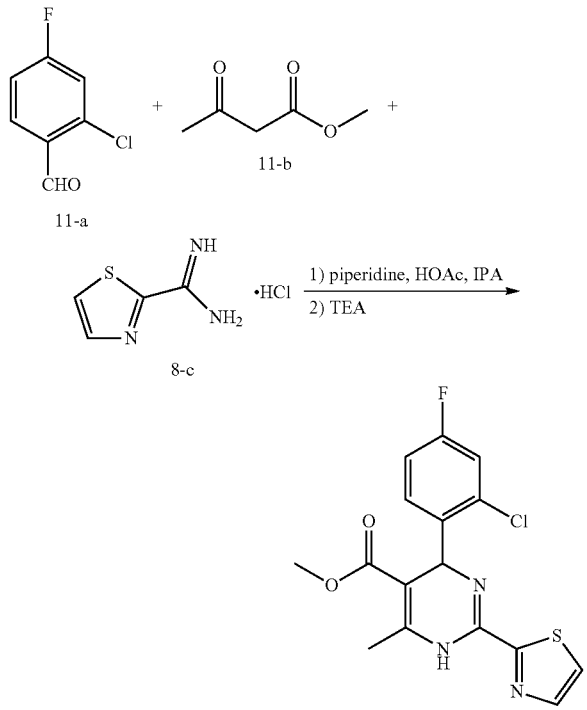

Example 11

A 1000 L glass-lined reactor equipped with mechanical stirrer, thermometer and nitrogen bubbler was charged 2-chloro-4-fluoro-benzaldehyde (30.8 kg, 194 mol, compound 11-a) and IPA (188.0 kg). To the solution was then added methyl acetoacetate (22.7 kg, 195 mol, compound 11-b) followed by addition of piperidine (1.74 kg, 20.4 mol) and acetic acid (1.32 kg, 22.0 mol). The reaction mixture was then heated to 43° C.-47° C. and stirred at such temperature for 5 hours. Then to the reaction mixture was added thiazole-2-carboxamidine hydrochloride salt (19.8 kg, 121.0 mol, compound 8-c) followed by addition of triethylamine (20.0 kg, 198.0 mol). The reaction mixture was heated to 80° C.-85° C. and stirred for 7 hours. After reaction was completed, the reaction mixture was cooled to 20° C.-25° C. and then added water (52.0 kg). The resulting suspension was stirred at 20° C.-25° C. for 2 hours. The solid was collected by centrifuge and washed with isopropanol/water (42 kg, v/v=10/3). The wet solid was dried in vacuum oven to afford Example 11 (35.05 kg, purity: 95.8%, Yield: 79.2%) as yellow solid. MS m/e=366.2 [M+H]$^+$.

Example 12

Preparation of (R)-4-(2-chloro-4-fluoro-phenyl)-6-methyl-2-thiazol-2-yl-1,4-dihydropyrimidine-5-carboxylic acid methyl ester mono (R)-(−)-1,1'-Binaphthyl-2,2'-diyl hydrogenphosphate salt mono MIBK solvate (Example 12)

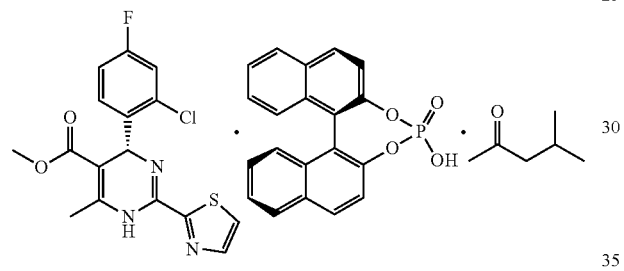

The title compound was prepared according to following scheme:

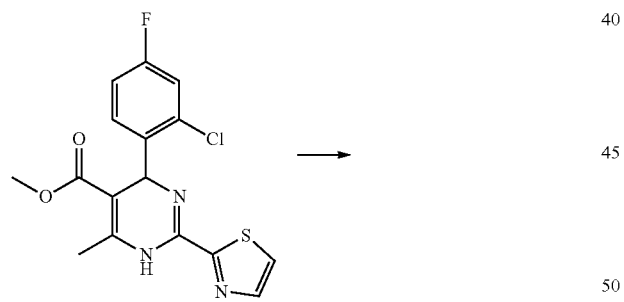

Example 11

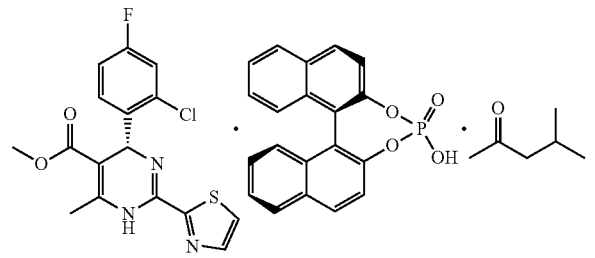

Example 12

A 1000 L reactor equipped with mechanical stirrer, thermometer and nitrogen bubbler was charged with 4-(2-chloro-4-fluoro-phenyl)-6-methyl-2-thiazol-2-yl-1,4-dihydropyrimidine-5-carboxylic acid methyl ester (23.8 kg, 65.06 mol, Example 11), MIBK (660 L) and purified water (6.6 L) at room temperature. The reaction mixture was stirred at room temperature for another 20 mins until all yellow solid was dissolved. After (R)-(−)-1,1'-Binaphthyl-2,2'-diyl hydrogen phosphate (18.1 kg, 52.05 mol) was added in one portion at room temperature, the reaction mixture was heated to 75° C. and the agitation was maintained for 14 hours. The reaction mixture was slowly cooled to 40° C. in 6 hours, then stirred at 40° C. for another 2 hours. The chiral salt was collected by centrifuge and rinsed with MIBK (50 L) for three times. The resulting solid was dried in vacuo at 55° C. for 24 hours to give Example 12 (21.75 kg, chiral purity: 99.45%, yield: 83.5%) as light yellow solid. MS m/e=366.2 [M+H].

Example 13

Preparation of 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Example 13)

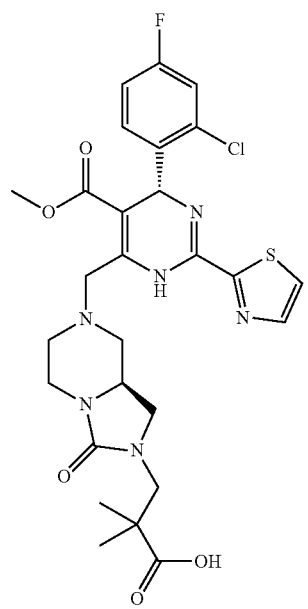

Example 13

The title compound was prepared according to following scheme:

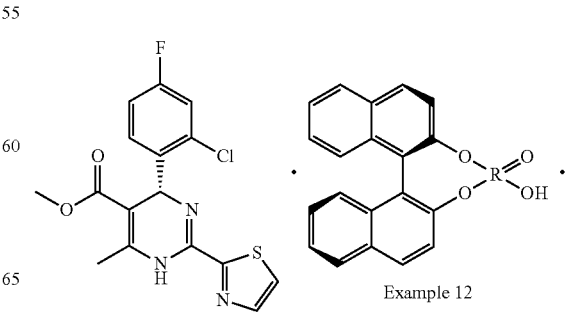

Example 12

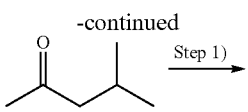

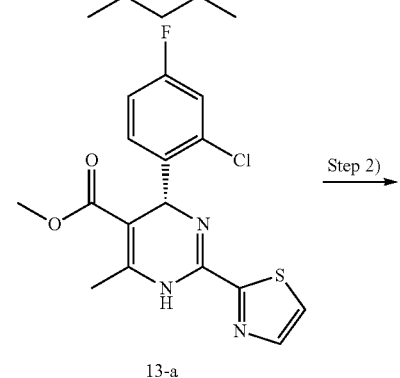

13-a

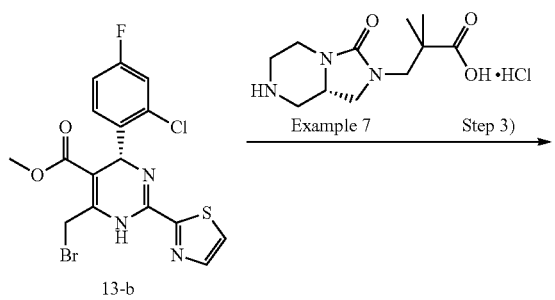

13-b

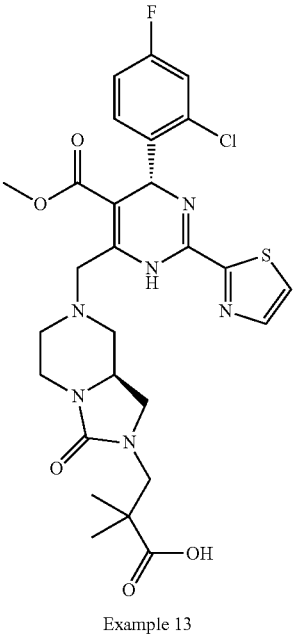

Example 13

Example 12

Step 1) Preparation of methyl (4R)-4-(2-chloro-4-fluoro-phenyl)-6-methyl-2-thiazol-2-yl-1,4-dihydropyrimidine-5-carboxylate (Compound 13-a)

A 250 mL flask equipped with magnetic stirrer, thermometer and nitrogen bubbler was charged with (R)-4-(2-chloro-4-fluoro-phenyl)-6-methyl-2-thiazol-2-yl-1,4-dihydropyrimidine-5-carboxylic acid methyl ester mono (R)-(−)-1,1'-Binaphthyl-2,2'-diyl hydrogenphosphate salt mono MIBK solvate (20.0 g, 24.6 mmol, compound 11-a) and dichloromethane (200 mL). To the reaction mixture was added aqueous NaOH solution (20 wt %, 5.40 g, 27.0 mmol) dropwise over 10 mins at 20° C.-30° C. The reaction mixture was stirred at 20° C.-30° C. for another 2.5 hours, then filtered, and the collected solid was washed with dichloromethane (20 mL). The filtrate was washed with water (50 mL). The combined organic phase was concentrated till dryness in vacuo. To the left residue was added fresh DCM (50 mL), the resulting solution was concentrated till dryness in vacuo and this process was repeated twice. Compound 13-a obtained as yellow oil was dissolved in DCM (100 mL) and used in the next step without further purification.

Step 2) Preparation of methyl (4R)-6-(bromomethyl)-4-(2-chloro-4-fluoro-phenyl)-2-thiazol-2-yl-1,4-dihydropyrimidine-5-carboxylate (Compound 13-b)

A 250 mL flask equipped with magnetic stirrer, thermometer and nitrogen bubbler was charged with a solution of methyl (4R)-4-(2-chloro-4-fluoro-phenyl)-6-methyl-2-thiazol-2-yl-1,4-dihydropyrimidine-5-carboxylate (24.6 mmol) in DCM (100 L) from step 1). To the reaction mixture, heated to 32° C.-37° C., was added $PBr_3$ (67 mg, 0.076 mmol) followed by addition of NBS (4.42 g, 24.6 mmol) in portions while maintaining the temperature. After 0.5 hour, additional batch of NBS (663 mg, 3.69 mmol) was added to the reaction mixture which was carefully monitored by HPLC until the conversion >95%. The resulting solution of compound 13-b was cooled to 10-20° C. and used directly for the next step. MS m/e=443.9/445.8/447.7 [M+H]$^+$.

Step 3) preparation of 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Example 13)

A 250 mL flask equipped with magnetic stirrer, thermometer and nitrogen bubbler was charged with a solution of methyl (4R)-6-(bromomethyl)-4-(2-chloro-4-fluoro-phenyl)-2-thiazol-2-yl-1,4-dihydropyrimidine-5-carboxylate in DCM from the last step. To the solution, cooled to 10° C.-20° C., was added 3-[(8aS)-3-oxo-1,5,6,7,8,8a-hexahydroimidazo[1,5-a]pyrazin-2-yl]-2,2-dimethyl-propanoic acid hydrochloride (5.09 g, 16.8 mmol, purity: 91.6 wt %, Example 7) followed by addition of triethanolamine (8.77 g, 26.8 mmol) in portions below 25° C. The reaction mixture was stirred at 20° C.-30° C. for 16 hours and then added water (30 mL), the aqueous layer was adjusted to pH=3-4 using $H_3PO_4$ (85 wt %). After phase separation, the organic phase was washed with acidic water (30 mL, $H_3PO_4$ solution with pH=2-3), then extracted with aqueous $H_3PO_4$ (35 wt %, 70 g) once and aqueous $H_3PO_4$ (35 wt %, 35 g) once. The combined aqueous layer was extracted with DCM (30 mL) and then, cooled to 0° C.-10° C., was added again fresh DCM (100 mL). After that, the aqueous layer was adjusted to pH=3-4 with aqueous NaOH solution (50 wt %, 30 g). After phase separation, the organic phase was washed with water (50 mL) and concentrated to dryness in vacuo. The residue was diluted with ethanol (25 mL) and concentrated to dryness in vacuo, then diluted again with ethanol (25 mL) and heated to 70-80° C. till all solid was dissolved. Water (25 mL) was added to previous solution via an addition funnel while maintaining inner temperature between 50° C. and 78° C. The reaction mixture was cooled to 25° C. over 3 hours and stirred at 25° C. for another hour. The solid was collected by filtration and washed with ethanol/water (v/v=1/1, 10 mL). The wet cake was dried in a vacuum oven (50° C./Ca. 0.1 Mpa with a nitrogen bleed) for 30 hours to afford the product Example 11 (4.28 g, purity: 99.3%; yield: 42%) as a light-yellow solid. $^1$H NMR (400 MHz, DMSO-$d^6$) δ 12.34 (s, 1H), 9.69 (s, 1H), 8.03 (d, J=3.2 Hz, 2H), 7.94 (d, J=3.2 Hz, 2H), 7.37-7.44 (m, 1H), 7.15-7.20 (m, 1H), 6.04 (s, 1H), 3.95 (d, J=16.8 Hz, 1H), 3.87 (d, J=16.8 Hz, 1H), 3.62-3.72 (m, 2H), 3.54 (s, 3H), 3.36-3.39 (m, 1H), 3.27 (d, J=14.0 Hz, 1H), 3.15 (d, J=14.0 Hz, 1H), 2.77-2.84 (m, 2H), 2.13-2.18 (m, 2H), 2.03 (t, J=10.8 Hz, 1H), 1.08 (m, 6H) MS m/e=606.2 [M+H]$^+$.

Example 14

The H$_3$PO$_4$ Concentration and Equivalent Screening in the Acid-Base Work-Up of Step 1)

The amount of H$_3$PO$_4$ in the acid-base work-up of step 1) is essential and carefully designed to get the maximum recovery of API and minimum impurities. The concentration and equivalent of H$_3$PO$_4$ in step 3) of Example 10 were screened according to Table 1. The major impurity was Impurity 2 shown below.

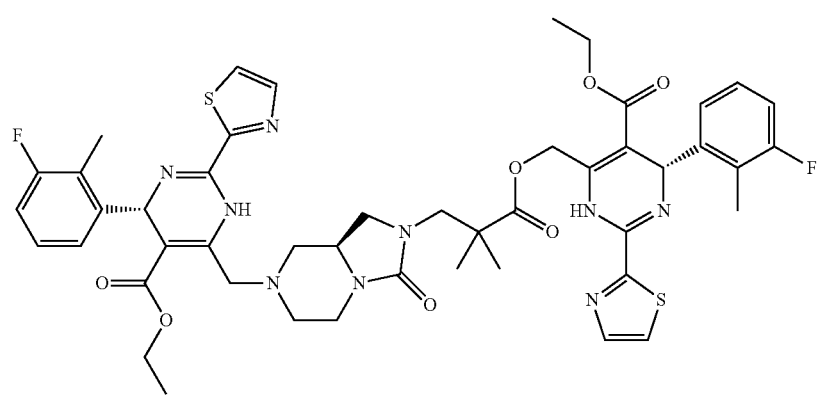

Impurity 2

After the initial H$_3$PO$_4$ solution wash (pH=3-4 and pH=2-3), the purity in organic layer was Product/Impurity 2(Rt$_{(impurity)}$=19.4 min)=71.9/1.38 (peak area %), the selected examples of further extractions with various H$_3$PO$_4$ concentration and equivalent were tested and shown in Table 1.

TABLE 1

H$_3$PO$_4$ concentration and equivalent screening

| concentration and equivalent of H$_3$PO$_4$ | Aqueous layer purity (peak area %) Product/Impurity 2 | Organic layer purity (peak area %) Product/Impurity 2 |
|---|---|---|
| 30 wt % H$_3$PO$_4$ 20 eq. | 95.2/0.0 | 14.0/4.6 |
| 35 wt % H$_3$PO$_4$ 10 eq. | 92.6/0.0 | 10.8/4.7 |
| 35 wt % H$_3$PO$_4$ 15 eq. | 93.7/0.1 | 5.4/5.0 |
| 35 wt % H$_3$PO$_4$ 20 eq. | 93.9/0.1 | 4.0/5.0 |
| 40 wt % H$_3$PO$_4$ 20 eq. | 92.3/0.5 | 3.9/3.9 |
| 45 wt % H$_3$PO$_4$ 20 eq. | 90.7/1.3 | 4.9/1.3 |

The above study was tested with following HPLC parameters shown in Table 2.

TABLE 2

HPLC parameters

| Instrument | Agilent 1260 HPLC system with DAD detector |
|---|---|
| Column | Waters Xbridge C8 (4.6 × 150 mm × 3.5 μm) |
| Oven temperature | 30° C. |
| Mobile phase | A: 0.12% TFA in water |
| | B: 0.12% TFA in ACN |

| Time (min) | A % | B % |
|---|---|---|
| Gradient program 0.00 | 80 | 20 |
| 15.00 | 50 | 50 |
| 20.00 | 10 | 90 |
| 25.00 | 10 | 90 |
| 25.01 | 80 | 20 |
| 30.00 | 80 | 20 |

| Flow rate | 1.0 mL/min |
|---|---|
| Detector | UV 299 nm |
| Nominal concentration | 0.5 mg/mL |
| Diluent | ACN:water = 1:1 |
| Injection volume | 10 μL |
| Run time | 30 min |

According to the results shown in Table 1, the amount of H$_3$PO$_4$ in the acid-base work-up of step 1) is directly related to the recovery of API and amount of impurities. Therefore the particular concentration of H$_3$PO$_4$ was 35 wt % to 40 wt % and 10-15 equivalent of compound of formula (XVII).

The invention claimed is:

1. A method for preparing a compound of formula (I),

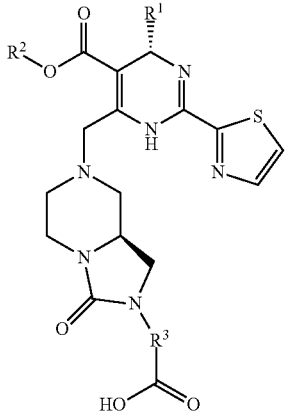
(I)

or a pharmaceutically acceptable salt or diastereomer thereof, the method comprising the following steps:

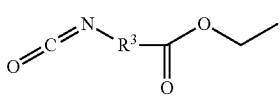
(III)

a) forming urea (V) via an addition reaction of isocyanate (III) and compound (IV);

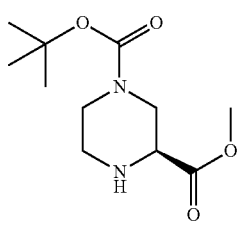
(IV)

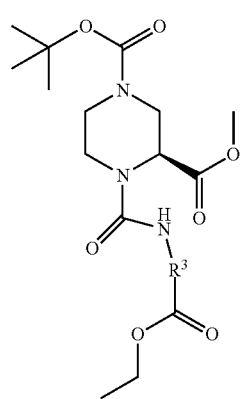
(V)

b) forming a compound of formula (VI) via a cyclization reaction of urea (V);

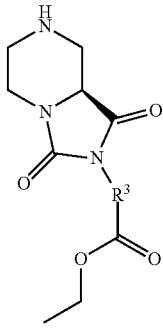
(VI)

c) forming a compound of formula (VII) by protecting the compound of formula (VI)

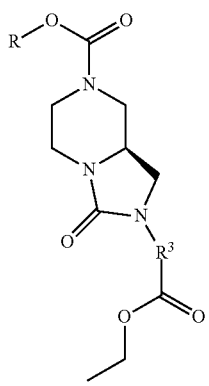
(VII)

wherein R is $C_{1-6}$alkyl;

d) forming a compound of formula (VIII) via selective reduction of compound (VII);

(VIII)

e) forming a compound of formula (IX) via hydrolysis of compound (VIII);

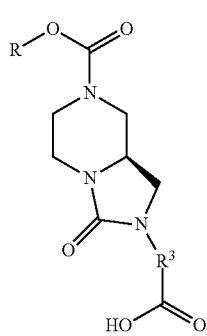

(IX)

f) forming a compound of formula (X) by de-protection of the compound of formula (IX);

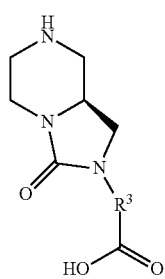

(X)

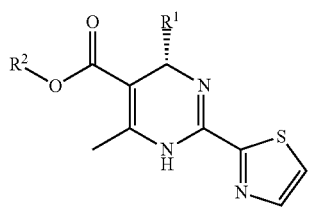

(XIV)

g) forming an enantiomeric salt (XVI) of a compound of formula (XIV) or a solvate thereof by addition of Acid in an organic solvent,

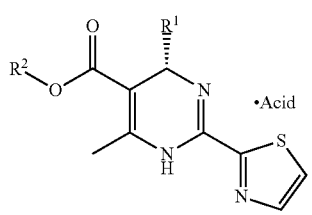

(XVI)

wherein Acid is an organic acid selected from: D-(+)-DTTA, L-DTTA, L-tartaric acid, D-DBTA, (+)-CSA, (S)-(+)-1,1'-Binaphthyl-2,2'-diyl hydrogen phosphate, and (R)-(−)-1,1'-Binaphthyl-2,2'-diyl hydrogen phosphate;

h) recovering an enantiomeric compound of formula (XVII) from compound (XVI);

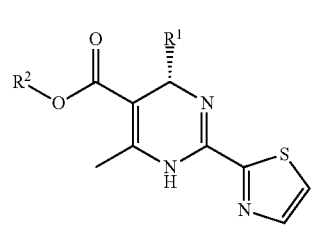

(XVII)

i) forming a compound of formula (XVIII) via bromination of compound (XVII);

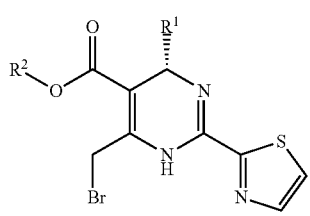

(XVIII)

j) forming the compound of formula (I) via a substitution reaction between compound (XVIII) and compound (X),

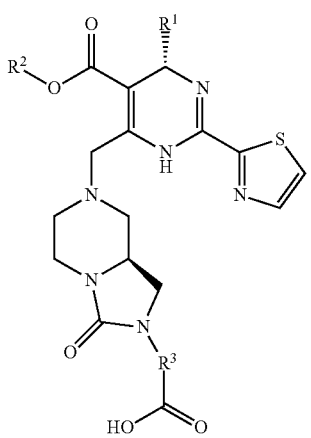

(I)

wherein:

R$^1$ is phenyl, which is unsubstituted or is substituted with one, two or three substituents independently selected from halogen and C$_{1-6}$alkyl;

R$^2$ is C$_{1-6}$alkyl; and

R$^3$ is —C$_x$H$_{2x}$—, wherein x is 1, 2, 3, 4, 5, 6 or 7.

2. The method according to claim 1, wherein:

R$^1$ is chlorofluorophenyl or methylchlorophenyl;

R$^2$ is methyl or ethyl; and

R$^3$ is dimethylethylene.

3. The method according to claim 1 wherein the compound of formula (I) is

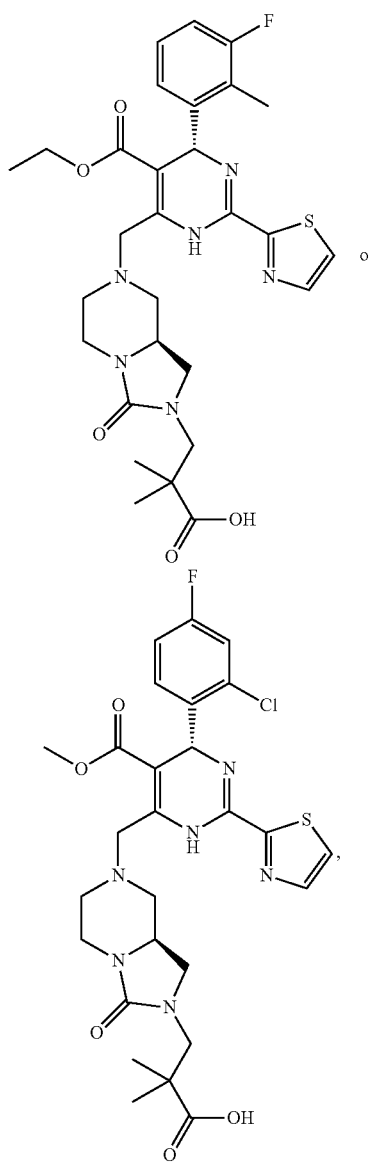

or a pharmaceutically acceptable salt or diastereomer thereof.

4. A method for preparing a compound of formula (X),

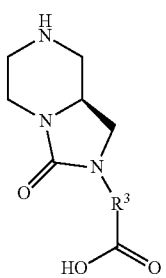
(X)

or a pharmaceutically acceptable salt, enantiomer or diastereomer thereof, the method comprising the following steps:

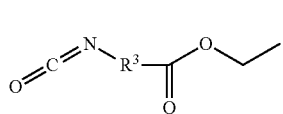
(III)

a) forming urea (V) via an addition reaction of isocyanate (III) and compound (IV);

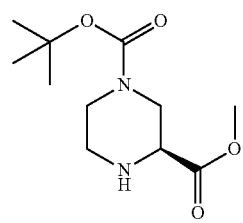
(IV)

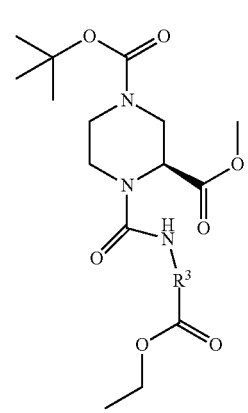
(V)

b) forming a compound of formula (VI) via a cyclization reaction of urea (V);

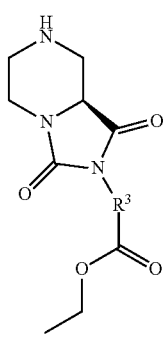
(VI)

c) forming a compound of formula (VII) by protecting the compound of formula (VI),

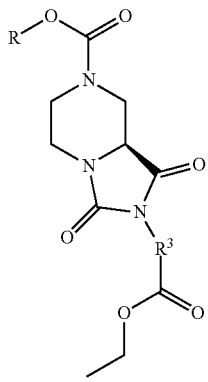
(VII)

wherein R is C<sub>1-6</sub> alkyl;

d) forming a compound of formula (VIII) via selective reduction of compound (VII);

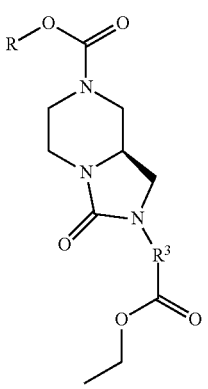
(VIII)

e) forming a compound of formula (IX) via hydrolysis of compound (VIII);

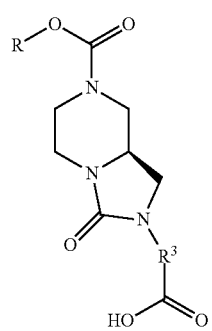
(IX)

f) forming a compound of formula (X) by de-protection of the compound of formula (IX),

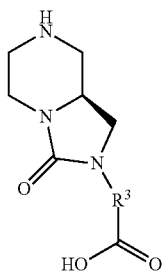
(X)

wherein:
R$^3$ is —C$_x$H$_{2x}$—; and
x is 1, 2, 3, 4, 5, 6 or 7.

5. The method according to claim 4, wherein R$^3$ is dimethylethylene.

6. The method according to claim 4 wherein the compound of formula (X) is

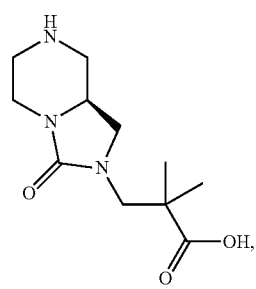 [SMILES: CC(C)(CN1C[C@@H]2CNCCN2C1=O)C(=O)O]

or a pharmaceutically acceptable salt or enantiomer thereof.

7. The method according to claim 1, wherein isocyanate (III) is prepared from a compound of formula (II) in the presence of a base in a solvent with a phosgene reagent, and

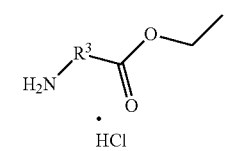
(II)

wherein the solvent is selected from 2-MeTHF, THF, IPAc, EA, toluene, and DCM.

8. The method of claim 7, wherein the base is selected from Na$_2$CO$_3$, NaHCO$_3$, K$_2$CO$_3$, Na$_3$PO$_4$ and K$_3$PO$_4$.

9. The method of claim 7, wherein the phosgene reagent is selected from phosgene, diphosgene and triphosgene.

10. The method of claim 1, wherein the formation of compound (VI) in b is performed in the presence of an acid in an organic solvent, wherein the solvent is selected from 2-MeTHF, IPAc, EA, toluene, DCM, methanol and ethanol.

11. The method of claim 10, wherein the acid is selected from boron trifluoride etherate, phosphoric acid, sulphuric acid, HBr and HCl.

12. The method of claim 1, wherein the formation of compound (VII) in c is performed in the presence of a base with a protecting reagent in a solvent, wherein the protecting reagent is selected from chloroformates and anhydrides.

13. The method of claim 12, wherein the solvent is selected from 2-MeTHF, THF, IPAc, EtOAc and DCM.

14. The method of claim 12, wherein the base is selected from TEA, DIPEA, $Na_2CO_3$, $NaHCO_3$, $K_2CO_3$, $Na_3PO_4$ and $K_3PO_4$.

15. The method of claim 1, wherein the formation of compound (VIII) in d) is performed in the presence of a catalytic Lewis acid and a reductive reagent, wherein the catalytic Lewis acid is selected from $InCl_3$, $YCl_3$, $ZnCl_2$, $Zn(OAc)_2$ and $BF_3$-$Et_2O$.

16. The method of claim 15, wherein the reductive reagent is selected from lithium aluminum hydride, sodium dihydro-bis-(2-methoxyethoxy)aluminate, borane dimethylsulfide, phenylsilane and borane tetrahydrofuran complex.

17. The method of claim 1, wherein compound (IX) in e) is isolated through a work-up procedure, wherein the work-up procedure comprises extraction with an organic solvent to remove the impurities, wherein the organic solvent is selected from THF, EA, IPAc, MTBE and toluene.

18. The method of claim 1, wherein the formation of compound (X) in f) is performed in the presence of an acid in a solvent, wherein the acid is selected from TFA, phosphoric acid, MSA, sulphuric acid, HBr and HCl.

19. The method of claim 18, wherein the solvent is selected from DCM, dioxane, EtOAc, IPAc, IPA, acetone, MIBK and a mixed solvent of MIBK and acetone.

20. The method of claim 18, wherein compound (X) in f) is isolated through recrystallization in a solvent, wherein the solvent is selected from acetonitrile, IPAc, MIBK, ethanol, acetone, a mixed solvent of acetone and methanol, and a mixed solvent of acetone and MIBK.

21. The method of claim 1, wherein the enantiomeric salt of the compound of formula (XVI) or solvate in g) is recrystallized in a solvent, wherein the solvent is selected from ethanol, MIBK, IPAc, toluene and MTBE.

22. The method of claim 1, wherein the formation of compound (I) in j) is performed in the presence of a base, wherein the base is selected from TMP, DIPEA, TEA, tripropylamine, N,N-dicyclohexylmethylamine, DBU, NMM, 2,6-lutidine, 1-methylimidazole, 1,2-dimethylimidazole, tetra methylpiperidine-4-ol, $Na_2CO_3$, $K_2CO_3$, $NaHCO_3$ and tris(2-hydroxylethyl)amine.

23. The method of claim 22, wherein compound (I) is purified in step j) through an acid-base work-up, wherein the acid used in the acid-base work-up is selected from HCl, HBr, $H_2SO_4$, $H_3PO_4$, MSA, toluene sulfonic acid and camphor sulfonic acid.

24. The method of claim 22, wherein the compound of formula (I) is recrystallized in j) in an organic solvent, wherein the organic solvent is selected from IPA, ethanol, EtOAc, IPAc, butyl acetate, toluene, MIBK, mixed solvent of acetone and water, mixed solvent of IPA and water, and mixed solvent of ethanol and water.

25. The method of claim 7, wherein the solvent is DCM.

26. The method of claim 7, wherein the base is aqueous $Na_2CO_3$ at a concentration of 5-25 wt. % or aqueous $K_2CO_3$ at a concentration of 5-30 wt. %.

27. The method of claim 7, wherein the base is aqueous $Na_2CO_3$ at a concentration of 10-15 wt. %.

28. The method of claim 7, wherein the phosgene reagent is triphosgene in an amount of 0.34-1.0 eq. of the compound of formula (II).

29. The method of claim 7, wherein the phosgene reagent is triphosgene in an amount of 0.34-0.45 eq. of the compound of formula (II).

30. The method of claim 10, wherein the solvent is ethanol.

31. The method of claim 11, wherein the acid is concentrated HCl.

32. The method of claim 12, wherein the protecting reagent is benzyl chloroformate or Boc anhydride.

33. The method of claim 12, wherein the protecting reagent is Boc anhydride.

34. The method of claim 13, wherein the solvent is THF or 2-MeTHF.

35. The method of claim 14, wherein the base is aqueous $Na_2CO_3$ or aqueous $NaHCO_3$.

36. The method of claim 15, wherein the Lewis acid is $BF_3$-$Et_2O$ in an amount of 0.05-1.1 eq. of compound (VII).

37. The method of claim 15, wherein the Lewis acid is $BF_3$-$Et_2O$ in an amount of 0.2 eq. of compound (VII).

38. The method of claim 16, wherein the reductive reagent is borane tetrahydrofuran complex, in an amount of 1.6-5.0 eq. of compound (VII).

39. The method of claim 16, wherein the reductive reagent is borane tetrahydrofuran complex, in an amount of 1.6-2.0 eq. of compound (VII).

40. The method of claim 17, wherein the organic solvent is IPAc.

41. The method of claim 18 wherein the acid is HCl.

42. The method of claim 19 wherein the solvent is MIBK.

43. The method of claim 20 wherein the solvent is acetone.

44. The method of claim 21 wherein the solvent is ethanol.

45. The method of claim 22, wherein the base is TMP or tris(2-hydroxylethyl)amine.

46. The method of claim 22, wherein the base is tris(2-hydroxylethyl)amine.

47. The method of claim 23, wherein the acid is aqueous $H_3PO_4$, at a concentration of 15 wt % to 60 wt %.

48. The method of claim 23, wherein the acid is aqueous $H_3PO_4$, at a concentration from 35 wt. % to 40 wt %.

49. The method of claim 47, wherein the amount of $H_3PO_4$ is 5-25 eq. of the compound of formula (XVII).

50. The method of claim 47, wherein the amount of $H_3PO_4$ is 10-15 eq. of the compound of formula (XVII).

51. The method of claim 24, wherein the solvent is a mixture of ethanol and water.

52. The method of claim 4, wherein the isocyanate (III) is prepared in the presence of a base in a solvent with phosgene reagent, wherein the solvent is selected from 2-MeTHF, THF, IPAc, EA, toluene, and DCM.

53. The method of claim 52, wherein the solvent is DCM.

54. The method of claim 52, wherein the base is aqueous $Na_2CO_3$ at a concentration of 5-25 wt % or aqueous $K_2CO_3$ at a concentration of 5-30 wt %.

55. The method of claim 4, wherein the formation of compound (VI) in b) is performed in the presence of an acid in an organic solvent, wherein the solvent is selected from 2-MeTHF, IPAc, EA, toluene, DCM, methanol and ethanol.

56. The method of claim 55, wherein the acid is selected from boron trifluoride etherate, phosphoric acid, sulphuric acid, HBr and HCl.

57. The method of claim 4, wherein the formation of compound (VII) in c) is performed in the presence of a base with a protecting reagent in a solvent, wherein the protecting reagent is selected from chloroformates and anhydrides.

58. The method of claim 57, wherein the solvent is selected from 2-MeTHF, THF, IPAc, EtOAc and DCM.

59. The method of claim 57, wherein the base is selected from TEA, DIPEA, $Na_2CO_3$, $NaHCO_3$, $K_2CO_3$, $Na_3PO_4$ and $K_3PO_4$.

60. The method of claim 4, wherein the formation of compound (VIII) in d) is performed in the presence of a catalytic Lewis acid and a reductive reagent, wherein the catalytic Lewis acid is selected from InCl$_3$, YCl$_3$, ZnCl$_2$, Zn(OAc)$_2$ and BF$_3$-Et$_2$O.

61. The method of claim 60, wherein the reductive reagent is selected from lithium aluminum hydride, sodium dihydro-bis-(2-methoxyethoxy)aluminate, borane dimethylsulfide, phenylsilane and borane tetrahydrofuran complex.

62. The method of claim 4, wherein the compound (IX) in e) is isolated through a work-up procedure, wherein the work-up procedure comprises extraction with an organic solvent to remove the impurities, wherein the organic solvent is selected from THF, EA, IPAc, MTBE and toluene.

63. The method of claim 4, wherein the formation of compound (X) in f) is performed in the presence of an acid in a solvent, wherein the acid is selected from TFA, phosphoric acid, MSA, sulphuric acid, HBr and HCl.

64. The method of claim 63, wherein the solvent is selected from DCM, dioxane, EtOAc, IPAc, IPA, acetone, MIBK and mixed solvent of MIBK and acetone.

65. The method of claim 64, wherein compound (X) in f) is isolated through recrystallization in a solvent, wherein the solvent is selected from acetonitrile, IPAc, MIBK, ethanol, acetone, mixed solvent of acetone and methanol, and mixed solvent of acetone and MIBK.

66. The method of claim 1, wherein compound (XIV) is synthesized by the following 3-stage scheme as a one-pot reaction in the presence of a catalyst and solvent:

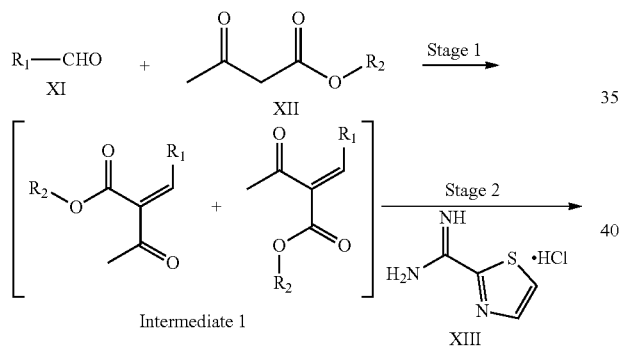

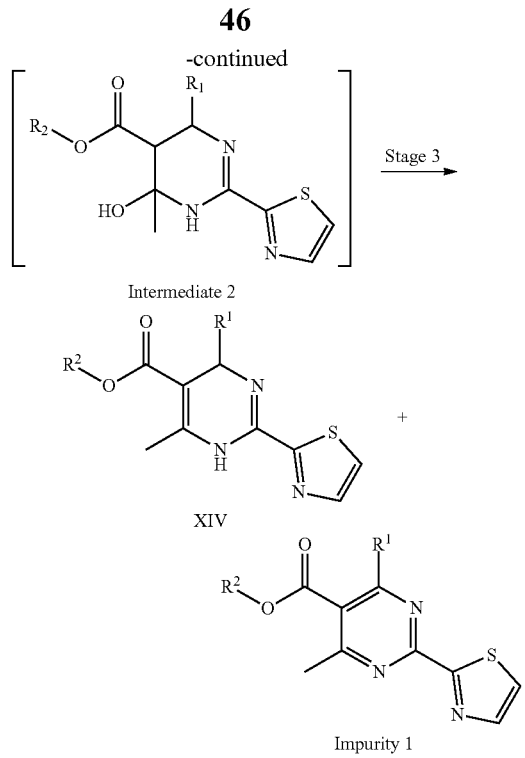

wherein:
the solvent is selected from methanol, ethanol, iso-propyl alcohol, t-BuOH, 2,2,2-trifluoro ethanol, and toluene;
the catalyst is selected from TEA, a mixture of TEA and AcOH, pyridine, a mixture of pyridine and AcOH, glycine, β-alanine, GABA, a mixture of DBU and AcOH, and a mixture of AcOH and piperidine;
Stage 2 is performed with a base selected from: TEA, DIPEA, DBU, NaEtO, and Na(t-BuO), wherein the base is added after compound (XII);
Stage 1 is performed at a temperature between 0° C. and 50° C.;
Stage 2 is performed at a temperature between 25° C. and 80° C.; and
Stage 3 is performed at a temperature between 50° C. and 80° C.

* * * * *